(12) United States Patent
Bollag et al.

(10) Patent No.: US 6,340,575 B1
(45) Date of Patent: Jan. 22, 2002

(54) METHODS AND COMPOSITIONS FOR TREATING ABNORMAL CELL GROWTH RELATED TO UNWANTED GUANINE NUCLEOTIDE EXCHANGE FACTOR ACTIVITY

(75) Inventors: Gideon Bollag, Hercules; Anne Crompton, San Francisco; Anne North, Pleasant Hill; William Roscoe, San Francisco; Sanju Sharma, Berkeley, all of CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/079,812

(22) Filed: May 15, 1998

Related U.S. Application Data
(60) Provisional application No. 60/049,879, filed on Jun. 17, 1997.

(51) Int. Cl.[7] .......................... C12P 21/00; C12N 15/63; C12N 15/85; C07H 21/04
(52) U.S. Cl. .................. 435/69.1; 435/320.1; 435/455; 536/23.1; 536/24.1
(58) Field of Search ............................ 435/69.1, 320.1, 435/325, 455; 536/23.1, 24.1

(56) References Cited

FOREIGN PATENT DOCUMENTS

WO   WO 98/23743   6/1998

OTHER PUBLICATIONS van Leeuwen et al. Onocogenic acitivity of Tiam–1 and Rac1 in NIH3T3 cells. Onogene. vol. 11:2215–2221, Dec. 1995.*
Habets et al. Sequence of the human invasion–inducing Tiam1 and gene, its conservation in evolution and its expression in tumor cell lines if different tissue origin. Oncogene. vol. 10:1371–1376, Mar. 1995.*
Marshall, E. Gene therapy's growing pains. Science vol. 269:1050–1055, Aug. 1995.*
Anderson, WF Human gene therapy. Nature vol. 392:25–30, Jun. 1998.*
Verma et al. Gene therapy—promises, problems and prospects. Nature vol. 389:239–242, Sep. 1997.*
Orkin et al. Report and recommendations of the panel to assess the NIH investment in research on gene therapy, Dec. 1995.*
Michleis et al. "A Role for Rac in Tiam1–induced membrane ruffling and invasion"Nature vol. 375, pp 338–340 (1995).
Habets et al. "Sequence of the human invasion–inducing TIAN1 gene, its converation in evolution and its expression in tumor cell lines of different tissue origin"Oncogene (1995) 10, 1371–1376.

* cited by examiner

*Primary Examiner*—Terry McKelvey
*Assistant Examiner*—William Sandals
(74) *Attorney, Agent, or Firm*—Gregory Giotta, Ph.D., J.D

(57) ABSTRACT

Methods and compositions are described that affect the GTPase activity of members of the Ras superfamily, preferably Rac, such compositions include guanine nucleotide exchange factors that modulate the GTPase activity, preferably in the presence of GEF enhancers, exemplary guanine nucleotide exchange factors being Rac-GEF and Tiam-1, which are encoded by certain nucleic acid sequences that are herein described, along with uses for the guanine nucleotide exchange factors and the nucleic acid sequences including screening for ligands which recognize Rac-GEF, regulators of Rac-GEF activity, and methods of treating pathological conditions associated or related to a Ras superfamily GTPase, including Rac.

15 Claims, 8 Drawing Sheets

Brain-Specific Sequence Map (1 > 198)   Site and Sequence
Enzymes:           All 478 enzymes (No Filter)
Settings:          Linear, Certain Sites Only, Standard Genetic Code GAATTCCCGCAGCCCGTTAGTCGCCCCCGACCCCAGCCCCAGGGCCCCGGCGTGGCCCCAGACCCGGCCCCGCCCCGCCCGCAGACCCTATGG
                                                                                                    97
——————— Brain Specific Sequence ———————
                  a.a. 1-66

Glu Phe Pro Gln Pro Val Ser Arg Pro Arg Pro Ser Pro Gly Pro Arg Arg Gly Pro Arg Pro Ser Thr Arg Pro Ala Ala Asp Pro Met

AGCTGCTGGCCGCTGCCTTCAGCGCCGCCTGCGCCGTGGACCACCGACAGTTCCACCTCGGAAAGCGACGCGGACTCGGCGGGGACACCTGCC
                                                                                                    194
——————— Brain Specific Sequence ———————
                  a.a. 1-66

Glu Leu Leu Ala Ala Ala Phe Ser Ala Ala Cys Ala Ala Val Asp His Asp Ser Ser Thr Ser Glu Ser Asp Ala Arg Asp Ser Ala Ala Gly His Leu Pro

CGGC
——→  198

FIGURE 2

SEQUENCE LISTING

<160> NUMBER OF SEQ ID NOS: 33

<210> SEQ ID NO 1
<211> LENGTH: 3171
<212> TYPE: DNA
<213> ORGANISM: Liver Rac GEF
<220> FEATURE:
<221> NAME/KEY: CDS
<222> LOCATION: Complement (76)..(2208)

<400> SEQUENCE: 1

```
tcactcaaac cagtgaagct tgggaaagtc attgacctcc agtcgttctg ctgagaaaca        60
tctggctcta tttcc atg gag acc agg gaa tct gaa gat ttg gaa aag acc       111
              Met Glu Thr Arg Glu Ser Glu Asp Leu Glu Lys Thr
                1               5                   10 cgg agg aaa tca gca agt gat caa tgg aac act gat aat gaa cca gcc       159
Arg Arg Lys Ser Ala Ser Asp Gln Trp Asn Thr Asp Asn Glu Pro Ala
         15                  20                  25 aag gtg aaa cct gag tta ctc cca gaa aaa gag gag act tct caa gct       207
Lys Val Lys Pro Glu Leu Leu Pro Glu Lys Glu Glu Thr Ser Gln Ala
     30                  35                  40 gac cag gat atc caa gac aaa gag cct cat tgc cac atc cca att aag       255
Asp Gln Asp Ile Gln Asp Lys Glu Pro His Cys His Ile Pro Ile Lys
 45                  50                  55                  60 aga aat tcc atc ttc aat cgc tcc ata aga cgc aaa agc aaa gcc aag       303
Arg Asn Ser Ile Phe Asn Arg Ser Ile Arg Arg Lys Ser Lys Ala Lys
                 65                  70                  75 gcc aga gac aac ccc gaa cgg aac gcc agc tgc ctg gca gat tca cag       351
Ala Arg Asp Asn Pro Glu Arg Asn Ala Ser Cys Leu Ala Asp Ser Gln
             80                  85                  90 gac aat gga aaa tct gta aat gag ccc ctg acc ttg aat atc ccc tgg       399
Asp Asn Gly Lys Ser Val Asn Glu Pro Leu Thr Leu Asn Ile Pro Trp
         95                 100                 105 agc aga atg cct cct tgc aga aca gca atg cag aca gac cca gga gcc       447
Ser Arg Met Pro Pro Cys Arg Thr Ala Met Gln Thr Asp Pro Gly Ala
    110                 115                 120
```

```
cag gaa atg agt gag tcg tcc tcc acc ccg gga aat ggg gcc acg ccc      495
Gln Glu Met Ser Glu Ser Ser Ser Thr Pro Gly Asn Gly Ala Thr Pro
125             130                 135                 140 gag gag tgg ccg gcc ctg gcc gac agc ccc acc acg ctc acc gag gcc      543
Glu Glu Trp Pro Ala Leu Ala Asp Ser Pro Thr Thr Leu Thr Glu Ala
                145                 150                 155 ctg cgg atg atc cac ccc att ccc gcc gac tcc tgg aga aac ctc att      591
Leu Arg Met Ile His Pro Ile Pro Ala Asp Ser Trp Arg Asn Leu Ile
        160                 165                 170 gaa caa ata ggg ctc ctg tat cag gaa tac cga gat aaa tcg act ctc      639
Glu Gln Ile Gly Leu Leu Tyr Gln Glu Tyr Arg Asp Lys Ser Thr Leu
            175                 180                 185 caa gaa atc gaa acc agg agg caa cag gat gca gaa ata gaa gac aat      687
Gln Glu Ile Glu Thr Arg Arg Gln Gln Asp Ala Glu Ile Glu Asp Asn
190                 195                 200 acc aat ggg tcc ccg gcc agt gag gac acc ccg gag gag gaa gaa gaa      735
Thr Asn Gly Ser Pro Ala Ser Glu Asp Thr Pro Glu Glu Glu Glu Glu
205                 210                 215                 220 gag gag gag gag gag gag ccg gcc agc cca cca gag agg aag act ctg      783
Glu Glu Glu Glu Glu Glu Pro Ala Ser Pro Pro Glu Arg Lys Thr Leu
                225                 230                 235 ccc cag atc tgc ctg ctc agt aac ccc cac tca agg ttc aac ctc tgg      831
Pro Gln Ile Cys Leu Leu Ser Asn Pro His Ser Arg Phe Asn Leu Trp
        240                 245                 250 cag gat ctt ccc gag atc cgg agc agc ggg gtg ctt gag atc cta cag      879
Gln Asp Leu Pro Glu Ile Arg Ser Ser Gly Val Leu Glu Ile Leu Gln
            255                 260                 265 cct gag gag att aag ctg cag gag gcc atg ttc gag ctg gtc act tcc      927
Pro Glu Glu Ile Lys Leu Gln Glu Ala Met Phe Glu Leu Val Thr Ser
270                 275                 280 gag gcg tcc tac tac aag agt ctg aac ctg ctc gtg tcc cac ttc atg      975
Glu Ala Ser Tyr Tyr Lys Ser Leu Asn Leu Leu Val Ser His Phe Met
285                 290                 295                 300 gag aac gag cgg ata agg aag atc ctg cac ccg tcc gag gcg cac atc     1023
Glu Asn Glu Arg Ile Arg Lys Ile Leu His Pro Ser Glu Ala His Ile
                305                 310                 315 ctc ttc tcc aac gtc ctg gac gtg ctg gct gtc agt gag cgg ttc ctc     1071
Leu Phe Ser Asn Val Leu Asp Val Leu Ala Val Ser Glu Arg Phe Leu
        320                 325                 330 ctg gag ctg gag cac cgg atg gag gag aac atc gtc atc tct gac gtg     1119
Leu Glu Leu Glu His Arg Met Glu Glu Asn Ile Val Ile Ser Asp Val
            335                 340                 345 tgt gac atc gtg tac cgt tat gcg gcc gac cac ttc tct gtc tac atc     1167
Cys Asp Ile Val Tyr Arg Tyr Ala Ala Asp His Phe Ser Val Tyr Ile
350                 355                 360 acc tac gtc agc aat cag acc tac cag gag cgg acc tat aag cag ctg     1215
Thr Tyr Val Ser Asn Gln Thr Tyr Gln Glu Arg Thr Tyr Lys Gln Leu
365                 370                 375                 380 ctc cag gag aag gca gct ttc cgg gag ctg atc gcg cag cta gag ctc     1263
Leu Gln Glu Lys Ala Ala Phe Arg Glu Leu Ile Ala Gln Leu Glu Leu
                385                 390                 395 gac ccc aag tgc agg ggg ctg ccc ttc tcc tcc ttc ctc atc ctg cct     1311
Asp Pro Lys Cys Arg Gly Leu Pro Phe Ser Ser Phe Leu Ile Leu Pro
        400                 405                 410 ttc cag agg atc aca cgc ctc aag ctg ttg gtc cag aac atc ctg aag     1359
Phe Gln Arg Ile Thr Arg Leu Lys Leu Leu Val Gln Asn Ile Leu Lys
            415                 420                 425
```

-continued

| | |
|---|---|
| agg gta gaa gag agg tct gag cgg gag tgc act gct ttg gat gct cac<br>Arg Val Glu Glu Arg Ser Glu Arg Glu Cys Thr Ala Leu Asp Ala His<br>430                             435                            440 | 1407 |
| aag gag ctg gaa atg gtg gtg aag gca tgc aac gag ggc gtc agg aaa<br>Lys Glu Leu Glu Met Val Val Lys Ala Cys Asn Glu Gly Val Arg Lys<br>445                             450                           455                       460 | 1455 |
| atg agc cgc acg gaa cag atg atc agc att cag aag aag atg gag ttc<br>Met Ser Arg Thr Glu Gln Met Ile Ser Ile Gln Lys Lys Met Glu Phe<br>                465                           470                       475 | 1503 |
| aag atc aag tcg gtg ccc atc atc tcc cac tcc cgc tgg ctg ctg aag<br>Lys Ile Lys Ser Val Pro Ile Ile Ser His Ser Arg Trp Leu Leu Lys<br>                480                           485                       490 | 1551 |
| cag ggt gag ctg cag cag atg tca ggc ccc aag acc tcc cgg acc ctg<br>Gln Gly Glu Leu Gln Gln Met Ser Gly Pro Lys Thr Ser Arg Thr Leu<br>495                             500                           505 | 1599 |
| agg acc aag aag ctc ttc cac gaa att tac ctc ttc ctg ttc aac gac<br>Arg Thr Lys Lys Leu Phe His Glu Ile Tyr Leu Phe Leu Phe Asn Asp<br>       510                            515                       520 | 1647 |
| ctg ctg gtg atc tgc cgg cag att cca gga gac aag tac cag gta ttt<br>Leu Leu Val Ile Cys Arg Gln Ile Pro Gly Asp Lys Tyr Gln Val Phe<br>525                             530                           535                       540 | 1695 |
| gac tca gct ccg cgg gga ctg ctg cgt gtg gag gag ctg gag gac cag<br>Asp Ser Ala Pro Arg Gly Leu Leu Arg Val Glu Glu Leu Glu Asp Gln<br>                545                           550                       555 | 1743 |
| ggc cag acg ctg gcc aac gtg ttc atc ctg cgg ctg ctg gag aac gca<br>Gly Gln Thr Leu Ala Asn Val Phe Ile Leu Arg Leu Leu Glu Asn Ala<br>                    560                           565                       570 | 1791 |
| gat gac cgg gag gcc acc tac atg cta aag gcg tcc tct cag agt gag<br>Asp Asp Arg Glu Ala Thr Tyr Met Leu Lys Ala Ser Ser Gln Ser Glu<br>575                             580                           585 | 1839 |
| atg aag cgt tgg atg acc tca ctg gcc ccc aac agg agg acc aag ttt<br>Met Lys Arg Trp Met Thr Ser Leu Ala Pro Asn Arg Arg Thr Lys Phe<br>590                             595                           600 | 1887 |
| gtt tcg ttc aca tcc cgg ctg ctg gac tgc ccc cag gtc cag tgc gtg<br>Val Ser Phe Thr Ser Arg Leu Leu Asp Cys Pro Gln Val Gln Cys Val<br>605                             610                           615                       620 | 1935 |
| cac cca tac gtg gct cag cag cca gac gag ctg acg ctg gag ctc gcc<br>His Pro Tyr Val Ala Gln Gln Pro Asp Glu Leu Thr Leu Glu Leu Ala<br>                    625                           630                       635 | 1983 |
| gac atc ctc aac atc ctg gac aag act gac gac ggg tgg atc ttt ggc<br>Asp Ile Leu Asn Ile Leu Asp Lys Thr Asp Asp Gly Trp Ile Phe Gly<br>                    640                           645                       650 | 2031 |
| gag cgt ctg cac gac cag gag aga ggc tgg ttc ccc agc tcc atg act<br>Glu Arg Leu His Asp Gln Glu Arg Gly Trp Phe Pro Ser Ser Met Thr<br>655                             660                           665 | 2079 |
| gag gag atc ttg aat ccc aag atc cgg tcc cag aac ctc aag gaa tgt<br>Glu Glu Ile Leu Asn Pro Lys Ile Arg Ser Gln Asn Leu Lys Glu Cys<br>670                             675                           680 | 2127 |
| ttc cgt gtc cac aag atg gat gac cct cag cgc agc cag aac aag gac<br>Phe Arg Val His Lys Met Asp Asp Pro Gln Arg Ser Gln Asn Lys Asp<br>685                             690                           695                       700 | 2175 |
| cgc agg aag ctg ggc agc cgg aat cgg caa tga cccccaccca ggggccagc<br>Arg Arg Lys Leu Gly Ser Arg Asn Arg Gln<br>                    705                           710 | 2228 |
| gggagcaggg cctgcatgag accccgacag aaggtggggg ggggggggggg ggctctggga | 2288 |
| agcacaggcc agcacctccc caggtggcag gatctggctt gggtgcccg gccctcatcc | 2348 |
| ctgcccacgc agtgagtgct catgtgtctt ggcccccttgc tcgcaaactg gataaagggt | 2408 |
| gcccaagcct ctcctgatgc atttgtaaac aagaaggttt cagcagtatt acaccacctc | 2468 |

-continued

```
cctcatgcct ccgagggggt ggaaggggt gggcacactc cagggccccc catgcccctg    2528
gcccccaggg attggaagag gctcccaacc cagagtgtcc ctgtgggagg caggcagaag    2588
gtgacaattg acacgatttc ctgcacgcgt cttcttttac cttggaagca gttagaattt    2648
accaggcaca gatgaggccg cccttgcctg acggagcttg atgagcagcc cttggtctcc    2708
ggttccagga ctgagagccc agctgcctct gcccacccct ccccaggcct ctgccagcct    2768
ctggctgcac ggtcaggccc tgccccatgg caggcctgcc agagcttggc tggggacccc    2828
tcccgcctct ggctccctga tgggctggat gtaacttgtg tcttctagcc ccttaaggag    2888
cccaggtgtt ttaaggaatg aattggtcac tgcatcttgt atcgattatg gttctgagaa    2948
aagcaaatat cggaattcct gcagcccggg aaatggggcc acgcccgagg agtggccggc    3008
cctggccgac agccccacca cgctcaccga ggccctgcgg atgatccacc ccattcccgc    3068
cgactcctgg agaaacctca ttgaacaaat agggctcctg tatcaggaat accgagataa    3128
atcgactctc caaaaaaaaa aaaaaaaaaa gatctttaat taa                      3171
```

<210> SEQ ID NO 2
<211> LENGTH: 710
<212> TYPE: PRT
<213> ORGANISM: Liver Rac GEF

<400> SEQUENCE: 2

```
Met Glu Thr Arg Glu Ser Glu Asp Leu Glu Lys Thr Arg Arg Lys Ser
 1               5                  10                  15

Ala Ser Asp Gln Trp Asn Thr Asp Asn Glu Pro Ala Lys Val Lys Pro
            20                  25                  30

Glu Leu Leu Pro Glu Lys Glu Thr Ser Gln Ala Asp Gln Asp Ile
        35                  40                  45

Gln Asp Lys Glu Pro His Cys His Ile Pro Ile Lys Arg Asn Ser Ile
     50                  55                  60

Phe Asn Arg Ser Ile Arg Arg Lys Ser Lys Ala Lys Ala Arg Asp Asn
 65                  70                  75                  80

Pro Glu Arg Asn Ala Ser Cys Leu Ala Asp Ser Gln Asp Asn Gly Lys
                85                  90                  95

Ser Val Asn Glu Pro Leu Thr Leu Asn Ile Pro Trp Ser Arg Met Pro
           100                 105                 110

Pro Cys Arg Thr Ala Met Gln Thr Asp Pro Gly Ala Gln Glu Met Ser
       115                 120                 125

Glu Ser Ser Ser Thr Pro Gly Asn Gly Ala Thr Pro Glu Glu Trp Pro
   130                 135                 140

Ala Leu Ala Asp Ser Pro Thr Thr Leu Thr Glu Ala Leu Arg Met Ile
145                 150                 155                 160

His Pro Ile Pro Ala Asp Ser Trp Arg Asn Leu Ile Glu Gln Ile Gly
               165                 170                 175

Leu Leu Tyr Gln Glu Tyr Arg Asp Lys Ser Thr Leu Gln Glu Ile Glu
           180                 185                 190

Thr Arg Arg Gln Gln Asp Ala Glu Ile Glu Asp Asn Thr Asn Gly Ser
       195                 200                 205

Pro Ala Ser Glu Asp Thr Pro Glu Glu Glu Glu Glu Glu Glu
   210                 215                 220

Glu Glu Pro Ala Ser Pro Pro Glu Arg Lys Thr Leu Pro Gln Ile Cys
225                 230                 235                 240
```

-continued

```
Leu Leu Ser Asn Pro His Ser Arg Phe Asn Leu Trp Gln Asp Leu Pro
                245                 250                 255
Glu Ile Arg Ser Ser Gly Val Leu Glu Ile Leu Gln Pro Glu Glu Ile
            260                 265                 270
Lys Leu Gln Glu Ala Met Phe Glu Leu Val Thr Ser Glu Ala Ser Tyr
        275                 280                 285
Tyr Lys Ser Leu Asn Leu Leu Val Ser His Phe Met Glu Asn Glu Arg
    290                 295                 300
Ile Arg Lys Ile Leu His Pro Ser Glu Ala His Ile Leu Phe Ser Asn
305                 310                 315                 320
Val Leu Asp Val Leu Ala Val Ser Glu Arg Phe Leu Leu Glu Leu Glu
                325                 330                 335
His Arg Met Glu Glu Asn Ile Val Ile Ser Asp Val Cys Asp Ile Val
            340                 345                 350
Tyr Arg Tyr Ala Ala Asp His Phe Ser Val Tyr Ile Thr Tyr Val Ser
        355                 360                 365
Asn Gln Thr Tyr Gln Glu Arg Thr Tyr Lys Gln Leu Leu Gln Glu Lys
    370                 375                 380
Ala Ala Phe Arg Glu Leu Ile Ala Gln Leu Glu Leu Asp Pro Lys Cys
385                 390                 395                 400
Arg Gly Leu Pro Phe Ser Ser Phe Leu Ile Leu Pro Phe Gln Arg Ile
                405                 410                 415
Thr Arg Leu Lys Leu Leu Val Gln Asn Ile Leu Lys Arg Val Glu Glu
            420                 425                 430
Arg Ser Glu Arg Glu Cys Thr Ala Leu Asp Ala His Lys Glu Leu Glu
        435                 440                 445
Met Val Val Lys Ala Cys Asn Glu Gly Val Arg Lys Met Ser Arg Thr
    450                 455                 460
Glu Gln Met Ile Ser Ile Gln Lys Lys Met Glu Phe Lys Ile Lys Ser
465                 470                 475                 480
Val Pro Ile Ile Ser His Ser Arg Trp Leu Leu Lys Gln Gly Glu Leu
                485                 490                 495
Gln Gln Met Ser Gly Pro Lys Thr Ser Arg Thr Leu Arg Thr Lys Lys
            500                 505                 510
Leu Phe His Glu Ile Tyr Leu Phe Leu Phe Asn Asp Leu Leu Val Ile
        515                 520                 525
Cys Arg Gln Ile Pro Gly Asp Lys Tyr Gln Val Phe Asp Ser Ala Pro
    530                 535                 540
Arg Gly Leu Leu Arg Val Glu Glu Leu Glu Asp Gln Gly Gln Thr Leu
545                 550                 555                 560
Ala Asn Val Phe Ile Leu Arg Leu Leu Glu Asn Ala Asp Asp Arg Glu
                565                 570                 575
Ala Thr Tyr Met Leu Lys Ala Ser Ser Gln Ser Glu Met Lys Arg Trp
            580                 585                 590
Met Thr Ser Leu Ala Pro Asn Arg Arg Thr Lys Phe Val Ser Phe Thr
        595                 600                 605
Ser Arg Leu Leu Asp Cys Pro Gln Val Gln Cys Val His Pro Tyr Val
    610                 615                 620
Ala Gln Gln Pro Asp Glu Leu Thr Leu Glu Leu Ala Asp Ile Leu Asn
625                 630                 635                 640
Ile Leu Asp Lys Thr Asp Asp Gly Trp Ile Phe Gly Glu Arg Leu His
                645                 650                 655
```

```
Asp Gln Glu Arg Gly Trp Phe Pro Ser Ser Met Thr Glu Glu Ile Leu
            660                 665                 670

Asn Pro Lys Ile Arg Ser Gln Asn Leu Lys Glu Cys Phe Arg Val His
        675                 680                 685

Lys Met Asp Asp Pro Gln Arg Ser Gln Asn Lys Asp Arg Arg Lys Leu
    690                 695                 700

Gly Ser Arg Asn Arg Gln
705                 710

<210> SEQ ID NO 3
<211> LENGTH: 20
<212> TYPE: DNA
<213> ORGANISM: Oligo

<400> SEQUENCE: 3
ggaggccatg ttcgagctgg                                        20

<210> SEQ ID NO 4
<211> LENGTH: 20
<212> TYPE: DNA
<213> ORGANISM: Oligonucleotide

<400> SEQUENCE: 4
gctgatcatc tgttccgtgc                                        20

<210> SEQ ID NO 5
<211> LENGTH: 37
<212> TYPE: DNA
<213> ORGANISM: Oligonucleotide

<400> SEQUENCE: 5
tcgaggaggt tataaatatg gaatacatgc caatgga                     37

<210> SEQ ID NO 6
<211> LENGTH: 37
<212> TYPE: DNA
<213> ORGANISM: Oligonucleotide

<400> SEQUENCE: 6
aatttccatt ggcatgtatt ccatatttat aacctcc                     37

<210> SEQ ID NO 7
<211> LENGTH: 21
<212> TYPE: DNA
<213> ORGANISM: Oligonucleotide

<400> SEQUENCE: 7
ccataaaacc atgggaaacg c                                      21

<210> SEQ ID NO 8
<211> LENGTH: 21
<212> TYPE: DNA
<213> ORGANISM: Oligonucleotide

<400> SEQUENCE: 8
ggttccgcgg aagagaagga t                                      21

<210> SEQ ID NO 9
<211> LENGTH: 21
<212> TYPE: DNA
<213> ORGANISM: Oligonucleotide
```

<400> SEQUENCE: 9
gactggcccg gggaactgag g                                    21

<210> SEQ ID NO 10
<211> LENGTH: 21
<212> TYPE: DNA
<213> ORGANISM: Oligonucleotide

<400> SEQUENCE: 10
tcggatgcgg ataagctgcg c                                    21

<210> SEQ ID NO 11
<211> LENGTH: 21
<212> TYPE: DNA
<213> ORGANISM: Oligonucleotide

<400> SEQUENCE: 11
gtgactggcg accttgttca t                                    21

<210> SEQ ID NO 12
<211> LENGTH: 26
<212> TYPE: DNA
<213> ORGANISM: Oligonucleotide

<400> SEQUENCE: 12
cggaattcag atttcgacac atgatc                               26

<210> SEQ ID NO 13
<211> LENGTH: 27
<212> TYPE: DNA
<213> ORGANISM: Oligonucleotide

<400> SEQUENCE: 13
tcgcccgggg caggtgacgc agtcaga                              27

<210> SEQ ID NO 14
<211> LENGTH: 49
<212> TYPE: DNA
<213> ORGANISM: Oligonucleotide

<400> SEQUENCE: 14
gatcccgggt catgtttctg gttctgggat ctcagtgttc agtttcctg      49

<210> SEQ ID NO 15
<211> LENGTH: 28
<212> TYPE: DNA
<213> ORGANISM: Oligonucleotide

<400> SEQUENCE: 15
cggaattcca tgggccgcct tggaatct                             28

<210> SEQ ID NO 16
<211> LENGTH: 27
<212> TYPE: DNA
<213> ORGANISM: Oligonucleotide

<400> SEQUENCE: 16
tcgcccgggc gtcagcagca cgattat                              27

<210> SEQ ID NO 17
<211> LENGTH: 67
<212> TYPE: DNA

```
<213> ORGANISM: Oligonucleotide

<400> SEQUENCE: 17
ggtgagcagt ttacactttc atatactccc tgtcatgtgc tttgaaggac tttctagggg    60
catcaag                                                              67

<210> SEQ ID NO 18
<211> LENGTH: 10
<212> TYPE: DNA
<213> ORGANISM: Oligonucleotide

<400> SEQUENCE: 18
gtcatgatgg                                                           10

<210> SEQ ID NO 19
<211> LENGTH: 15
<212> TYPE: DNA
<213> ORGANISM: Oligonucleotide

<400> SEQUENCE: 19
tccatcatga cggcc                                                     15

<210> SEQ ID NO 20
<211> LENGTH: 37
<212> TYPE: DNA
<213> ORGANISM: Oligonucleotide

<400> SEQUENCE: 20
cttgaattcc accatggaaa tctgtccaaa agtcact                             37

<210> SEQ ID NO 21
<211> LENGTH: 27
<212> TYPE: DNA
<213> ORGANISM: Oligonucleotide

<400> SEQUENCE: 21
tcgcccgggc gtcagcagca cgattat                                        27

<210> SEQ ID NO 22
<211> LENGTH: 21
<212> TYPE: DNA
<213> ORGANISM: Oligonucleotide

<400> SEQUENCE: 22
catggaccag aacccatctc c                                              21

<210> SEQ ID NO 23
<211> LENGTH: 20
<212> TYPE: DNA
<213> ORGANISM: Oligonucleotide

<400> SEQUENCE: 23
tgaggagatg ggttctggtc                                                20

<210> SEQ ID NO 24
<211> LENGTH: 20
<212> TYPE: DNA
<213> ORGANISM: Oligonucleotide

<400> SEQUENCE: 24
gccagaacca gaaacatgac                                                20
```

```
<210> SEQ ID NO 25
<211> LENGTH: 24
<212> TYPE: DNA
<213> ORGANISM: Oligonucleotide

<400> SEQUENCE: 25
ccgggtcatg tttctggttc tggc                                              24

<210> SEQ ID NO 26
<211> LENGTH: 30
<212> TYPE: DNA
<213> ORGANISM: Oligonucleotide

<400> SEQUENCE: 26
gaggaattcg atctgagcat gggagacctg                                        30

<210> SEQ ID NO 27
<211> LENGTH: 34
<212> TYPE: DNA
<213> ORGANISM: Oligonucleotide

<400> SEQUENCE: 27
ctgctcgagc tacttatcac gcaggattga aatg                                   34

<210> SEQ ID NO 28
<211> LENGTH: 30
<212> TYPE: DNA
<213> ORGANISM: Oligonucleotide

<400> SEQUENCE: 28
caggaattcg tgcgcaaggc cggcgccctg                                        30

<210> SEQ ID NO 29
<211> LENGTH: 33
<212> TYPE: DNA
<213> ORGANISM: Brain Specific Nucleotide for Rac-GEF

<400> SEQUENCE: 29
gtgctcgagc tacgcagtgg cgcaggcaga gtg                                    33

<210> SEQ ID NO 30
<211> LENGTH: 198
<212> TYPE: DNA
<213> ORGANISM: Glu-Epitope Tag
<220> FEATURE:
<221> NAME/KEY: CDS
<222> LOCATION: Complement (1)..(198)

<400> SEQUENCE: 30 gaa ttc ccg cag ccc gtt agt cgc ccc cga ccc agc cca ggg ccc cgg        48
Glu Phe Pro Gln Pro Val Ser Arg Pro Arg Pro Ser Pro Gly Pro Arg
 1               5                  10                  15 cgt ggc ccc aga ccc ggc ccc agc acc cgc ccc gcc gca gac cct atg        96
Arg Gly Pro Arg Pro Gly Pro Ser Thr Arg Pro Ala Ala Asp Pro Met
             20                  25                  30 gag ctg ctg gcc gct gcc ttc agc gcc gcc tgc gcc gtg gac cac gac       144
Glu Leu Leu Ala Ala Ala Phe Ser Ala Ala Cys Ala Val Asp His Asp
         35                  40                  45 agt tcc acc tcg gaa agc gac gcg cgc gac tcg gcg gcg gga cac ctg       192
Ser Ser Thr Ser Glu Ser Asp Ala Arg Asp Ser Ala Ala Gly His Leu
     50                  55                  60 ccc ggc                                                                198
Pro Gly
 65
```

```
<210> SEQ ID NO 31
<211> LENGTH: 66
<212> TYPE: PRT
<213> ORGANISM: Glu-Epitope Tag

<400> SEQUENCE: 31

Glu Phe Pro Gln Pro Val Ser Arg Pro Arg Pro Ser Pro Gly Pro Arg
 1               5                  10                  15

Arg Gly Pro Arg Pro Gly Pro Ser Thr Arg Pro Ala Ala Asp Pro Met
            20                  25                  30

Glu Leu Leu Ala Ala Ala Phe Ser Ala Ala Cys Ala Val Asp His Asp
        35                  40                  45

Ser Ser Thr Ser Glu Ser Asp Ala Arg Asp Ser Ala Ala Gly His Leu
    50                  55                  60

Pro Gly
 65

<210> SEQ ID NO 32
<211> LENGTH: 11
<212> TYPE: PRT
<213> ORGANISM: Glu-Epitope Tag

<400> SEQUENCE: 32

Met Glu Tyr Met Pro Met Glu Ile Arg His Asp
 1               5                  10

<210> SEQ ID NO 33
<211> LENGTH: 5
<212> TYPE: PRT
<213> ORGANISM: KT3 EPITOPE TAG

<400> SEQUENCE: 33

Pro Glu Pro Glu Thr
 1               5
```

METHODS AND COMPOSITIONS FOR TREATING ABNORMAL CELL GROWTH RELATED TO UNWANTED GUANINE NUCLEOTIDE EXCHANGE FACTOR ACTIVITY

This application claims priority from U.S. Provisional Application No. 60/049,879 filed Jun. 17, 1997.

FIELD OF THE INVENTION

This invention is in the field of molecular biology, and involves methods and compositions for regulating unwanted cell growth through the regulation of the activity of certain guanine nucleotide exchange factors.

BACKGROUND OF THE INVENTION

Ras is a member of a superfamily of GTPases that regulate diverse signaling pathways. Ras itself has been shown to be involved in regulating cell growth and differentiation (See, Boguski, M. S. and McCormick, F. (1993) *Nature* 366, 643–654). A subfamily of Ras consists of Rho, Rac, and Cdc42. These GTPase have also been shown to be involved in regulating cell growth, particularly as relating to cellular transformation, as well as controlling the formation of focal contacts and alterations in the actin cytoskeleton which occur upon growth factor stimulation (See, Coso, O. A., Chiariello, M., Yu, J.-C., Teramoto, H., Crespo, P., Xu, N., Miki, T. and Gutkind, J. S. (1995) *Cell* 81, 1137–1146; Hill, C. S., Wynne, J. and Treisman, R. (1995) *Cell* 81, 1159–1170; Kozma, R., Ahmed, S., Best, A. and Lim, L. (1995) *Mol. Cell. Biol.* 15, 1942–1952; Minden, A., Lin, A., Claret, F.-X., Abo, A. and Karin, M. (1995) *Cell* 81, 1147–1157; Nobes, C. D. and Hall, A. (1995) *Cell* 81, 53–62; Olson, M. F., Ashworth, A. and Hall, A. (1995) *Science* 269, 1270–1272). Common to all Ras family members is their ability to cycle between inactive (GDP bound) and active (GTP bound) states. In this regard, these GTPases act as molecular switches, capable of processing information and then disseminating that information to control a specific pathway.

This property of cycling between GTP and GDP states has provided a means to identify and purify proteins which regulate the nucleotide state of Ras and Ras related GTPases. See, Boguski, M. S. and McCormick, F. (1993) *Nature* 366, 643–654.

By monitoring the hydrolysis of GTP to GDP, GTPase activating proteins (GAPs) have been characterized for many members of the Ras family. See, Boguski, M. S. and McCormick, F. (1993) *Nature* 366, 643–654; Barfod, E. T., Zheng, Y., Kuang, W.-J., Hart, M. J., Evans, T., Cerione, R. A. and Ashkenaz, A. (1993) *J. Biol. Chem.* 268, 26059–26062; Lamarche, N. and Hall, A. (1994) *Trends Genet.* 10, 436–440; Cerione, R. A. and Zheng, Y. (1996) *Current Opinion in Cell Biology* 8, 216–222. The latter reference provides a good discussion of the properties of those proteins that affect the guanine nucleotide state of Ras and Ras related proteins. Guanine nucleotide dissociation inhibitors (GDIs) were identified based on their ability to inhibit the dissociation of GDP. It has subsequently been determined that they also bind to the GTP state, inhibiting the intrinsic and GAP stimulated GTP hydrolysis. See, Boguski, M. S. and McCormick, F. (1993) *Nature* 366, 643–654. In general, GAPs and effectors have a high affinity for the GTP-bound state, while GDI proteins bind most tightly to the GDP-bound state. These properties have been exploited to purify effectors for Cdc42Hs (See, Bagrodia, S., Taylor, S. J., Creasy, C. L., Chernoff, J. and Cerione, R. A. (1995) *J. Biol. Chem.* 270, 22731–22737; Manser, E., Leung, T., Salihuddin, H., Zhao, Z.-s. and Lim, L. (1994) *Nature* 367, 40–46; Martin, G. A., Bollag, G., McCormick, F. and Abo, A. (1995) *EMBO J.* 14, 1970–1978), Ras (See, Moodie, S. A., Willumsen, B. M., Weber, M. J. and Wolfman, A. (1993) *Science* 260, 1658–1661; Rodriguez-Viciana, P., Warne, P. H., Dhand, R., Vanhaesebroeck, B., Gout, I., Fry, M. J., Waterfield, M. D. and Downward, J. (1994) *Nature* 370, 527–532) and Rho (See, Leung, T., Manser, E., Tan, L. and Lim, L. (1995) *J. Biol. Chem.* 270, 29051–29054; Watanabe, G., Saito, Y., Madaule, P., Ishizaki, T., Fujisawa, K., Morii, N., Mukai, H., Ono, Y., Kakizuki, A. and Narumiya, S. (1996) *Science* 271, 645–648). An affinity approach has also been employed with Cdc42Hs-GTP and has led to the characterization of IQGAP 1, a potential mediator for observed cytoskeletal events induced by Cdc42. See, Hart, M. J., Callow, M., Souza, B. and Polakis, P. (1996) *EMBO J.* 15, 2997–3005.

A modification of this affinity approach can also be used to identify and purify guanine nucleotide exchange factors (GEFs). GEFs can be distinguished from other regulatory proteins by their ability to interact preferentially with the nucleotide-depleted state of G-proteins. See, Hart, M. J., Eva, A., Zangrilli, D., Aaronson, S. A., Evans, T., Cerione, R. A. and Zheng, Y. (1994) *J. Biol. Chem.* 269, 62–65; Mosteller, R. D., Han, J. and Broek, D. (1994) *Mol. Cell. Biol.* 14, 1104–1112. By stimulating the dissociation of GDP and subsequent binding of GTP, GEFs play an important role in the activation of Ras-like proteins. For example, Ras is converted to its GTP-bound form by the growth-factor stimulated translocation of Sos, a Ras-specific GEF. See, Buday, L. and Downward, J. (1993) *Cell* 73, 611–620.

The characterization of GEFs that specifically activate Rac family members will help elucidate signalling pathways in which these GTPases participate, and thus lead to a better understanding of the molecular basis of cell growth. This, in turn, will enable the identification of drugs for preventing or treating diseases where uncontrolled cell growth is the cause. Because Rac plays a key role in signal transduction and cell growth, the identification and properties of Rac GEFs is presently receiving considerable scientific attention. One such Rac GEF is known, Tiam-1. See, Michiels, F., Habets, G. G., Stam, J. C., van der Kammen, R. A., and Collard, J. G. (1995) *Nature* 375, 338–340. See also, Eva, A. and Aaronson, S. A. (1985) *Nature* 316, 273–275; Toksoz, D. and Williams, D. A. (1994) *Oncogene* 9, 621–628.

DESCRIPTION OF THE INVENTION

The present invention relates to all aspects of a guanine exchange factor (GEF), in particular, a Rac-GEF. A GEF modulates cell signaling pathways, both in vitro and in vivo, by modulating the activity of a GTPase. By way of illustration, a Rac-GEF, which modulates the activity of a Rac GTPase, is described. However, the present invention relates to other GEFs, especially other Rac-GEFs.

The present invention preferably relates to an isolated Rac-GEF polypeptide characterized by having a Src homology, Dbl homology and pleckstrin homology domains, and variants thereof, or fragments of such polypeptides, nucleic acids coding for such Rac-GEFs or nucleic acid fragments, and derivatives of the polypeptides and nucleic acids.

The invention also relates to methods of using such polypeptides, nucleic acids, or derivatives thereof, e.g., in therapeutics, diagnostics, and as research tools.

Another aspect of the present invention involves antibodies and other ligands which recognize the invention Rac-GEF, regulators of Rac-GEF activity and other GEFs, and methods of treating pathological conditions associated or related to such Rac GTPase.

The invention also relates to methods of testing for and/or identifying agents which regulate GEF by measuring their effect on GEF activity, e.g., in binding to a GTPase and/or nucleotide exchange activity.

The invention also relates to methods of assaying for GEF activity, preferrably using activators of GEF activity.

These and other aspects of the invention will become apparent upon a full considertion of the following disclosure.

BRIEF DESCRIPTION OF THE DRAWINGS

FIG. 2 shows the brain specific nucleotide and protein sequence for a Rac-GEF SEQ ID NO:30(SEQ ID NO:31).

DETAILED DESCRIPTION OF THE INVENTION

Figure 1:
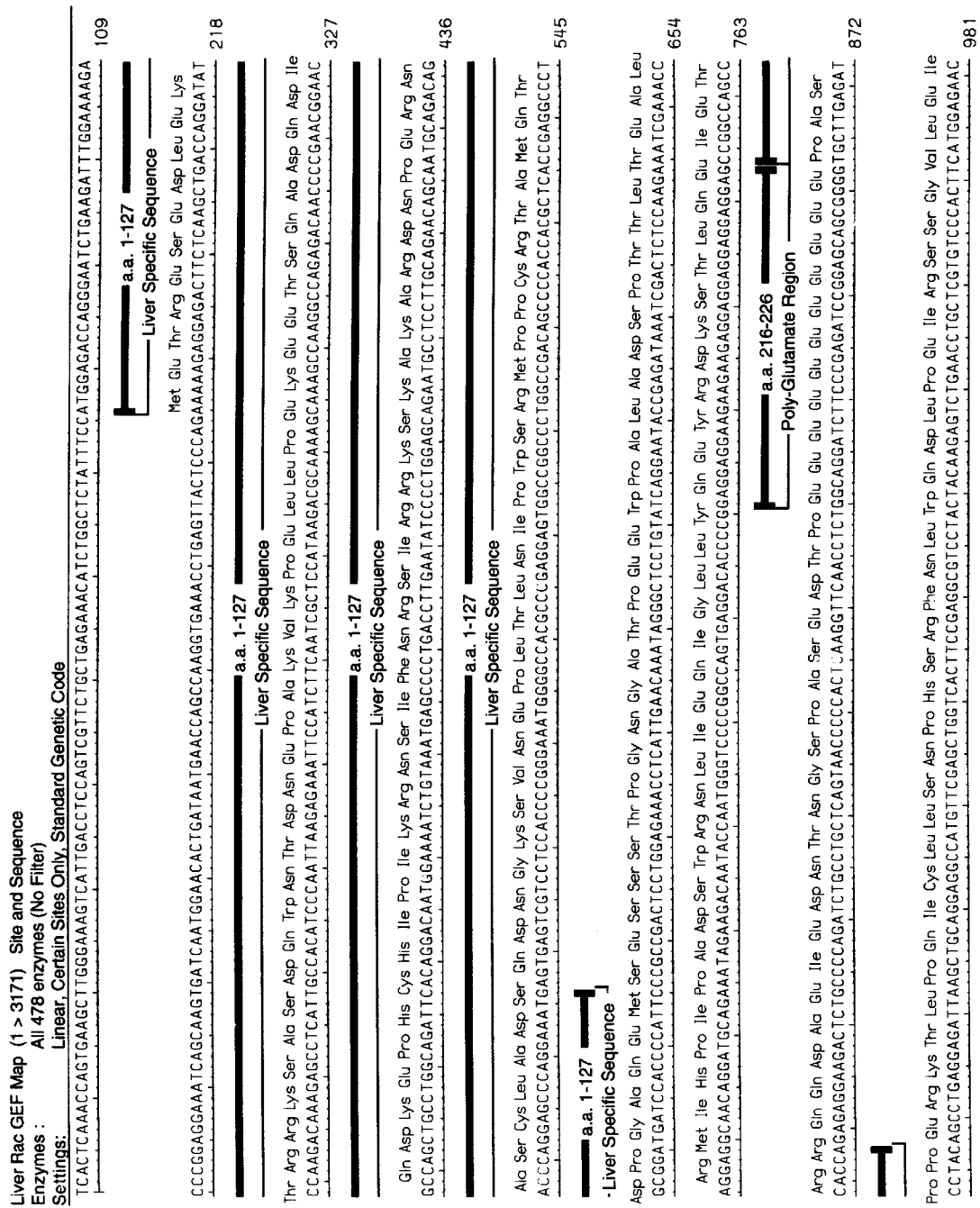
FIG. 1 shows the complete nucleotide sequence (SEQ ID NO: 1) and deduced amino acid sequence (SEQ ID NO:2) for a polypeptide encoded for by a human GEF-Rac gene.

In accordance with the present invention, a novel polypeptide and nucleic acid coding for a Rac-GEF has been identified and isolated. Alternate variants of the molecule have also beeen identified. As used herein, Rac-GEF means a polypeptide, or a nucleic acid coding for a Rac-GEF polypeptide, which polypeptide has a specific binding affinity for a guanine nucleotide-depleted state of G-proteins (in particular Rac), a guanine nucleotide exchange activity, an oncogenic transforming activity, and an immunogenic activity. By specific binding affinity, it is meant that the polypeptide has a binding preference for the nucleotide-depleted state of the G-protein, in contrast, e.g., to the GDP- or GTP-bound state of the G-protein which is preferentially bound by other regulatory proteins. By guanine nucleotide exchange activity, it is meant that the polypeptide stimulates or catalyzes the dissociation of GDP from a G-protein, such as Rac, and subsequent binding of GTP. By cellular oncogenic transforming activity, it is meant that introduction of a nucleic acid coding for Rac-GEF into a cell line, e.g., NIH 3T3 cells, confers a transformed phenotype on such cells. A transformed phenotype can be measured by foci formation, e.g., as characterized and described by Eva and Aaronson, Nature, 316:273–276, 1985. Immunogenic activity means that the polypeptide binds to Rac-GEF specific antibodies or is capable of eliciting an immune response specific for a Rac-GEF. Immunogenic activities are discussed below. The above-mentioned activities of a Rac-GEF polypeptide can be assayed, e.g., as described below in the examples or according to methods which the skilled worker would know. A Rac-GEF polypeptide, or corresponding nucleic acid coding for it, means a polypeptide which can be isolated from a natural source. It therefore includes naturally-occurring normal and mutant alleles. Natural sources include, e.g., living cells obtained from tissues and whole organisms, and cultured cell lines.

To identify a human gene that encodes a Rac-GEF, we performed a search of the EST data base for Dlb homologs. The search was performed using an amino acid sequence (residues 1–519) encoded by the human TIM protein (Chan et al., 1994, Ocogene, Vol. 9, pages 1057–1063). A single clone was identified, and the plasmid encoding this insert was purchased via the I.M.A.G.E. Consortium (Research Genetics). Using this cDNA as template, a 511-bp $^{32}$P-labelled PCR product was produced using oligos 5'-GGAGGCCATGTTCGAGCTGG-3' (SEQ ID No:3) and 5'-GCTGATCATCTGTTCCGTGC-3' SEQ ID No:4 (5' and 3' primers, respectively) and $^{32}$P labelled nucleotides. This labeled PCR fragment was used as a probe to screen approximately $4\times10^5$ clones of a human fetal brain Lambda ZAP cDNA library (Stratagene). A clone with an insert of 2.6-kb was isolated, and the complete DNA sequence of this clone was determined and shown to have a single open reading frame of 1950-bp that is predicted to encode a 650-amino acids protein with a calculated molecular mass of 74.7 kDa. A comparision of the DNA sequences of the EST insert to the fetal brain cDNA revealed a 72 base pair insert in the fetal brain sequence. The insert is in the DH domain.

As discussed more in the Examples, Northern analysis revealed a 3.5 kb transcript in brain tissue and a 4 kb transcript in liver. Consequently, using the additional sequence identified from the 2.6-kb sequence that was not present in EST #167059 we identified another EST (#109922) that had been isolated from a human cDNA liver library. The plasmid containing this insert was also obtained, and the insert sequenced which revealed an initiating methionine.

FIG. 1 (SEQ ID NO(s): 1 and 2) show the alignment of the full length liver nucleotide cDNA sequence, with its deduced amino acid sequence, respectively. It is note worthy that this sequence has an additional 126 amino acids which differ from the amino-terminal 66 amino acids of the 2.6 kb brain cloned (FIG. 2 SEQ ID No. 30 (SEQ ID NO:31)). Also shown in the figure are various domains, including the Src homology 3, Dbl homology and pleckstrin homology domains. It, or its corresponding gene, can be isolated from natural sources. Characterization of a human Rac-GEF is described below and in the examples.

It is noteworthy that because of the protein-protein interactive properties of the Src homology 3 domain, ligands that bind to this domain may be identified, for example, by screening an expression library, that affect Rac-GEF activity. Such ligands would have medical applications.

The present invention also relates to polypeptide fragments of Rac-GEF. The fragments are preferably biologically-active. By biologically-active, it is meant that the polypeptide fragment possesses an activity in a living system or with components of a living system. Biological-activities include: a specific binding affinity for a guanine nucleotide-depleted state of G-proteins, in particular Rac, a guanine nucleotide exchange activity, an oncogenic transforming activity, an immunogenic activity, modulating the binding between a Rac-GEF and a Rac GTPase, or acting as an agonist or antagonist of Rac GTPase activity. Such activities can be assayed routinely, e.g., according to the methods described above and below. Various fragments can be prepared. See the examples below for further discussion. Fragments can also be selected in which one or more of the mentioned activities are eliminated or altered when compared to Rac-GEF. As described in the examples, such fragments can be prepared routinely, e.g., by recombinant means or by proteolytic cleavage of isolated polypeptides, and then assayed for a desired activity.

The present invention also relates to a human Rac-GEF specific amino acid sequence as set forth in FIG. 1 (SEQ ID NO: 2): A clone encoding such sequence, 128 to 710 amino acids and also containing 66 divergent amino acids as shown in FIG. 2 SEQ ID NO. 30 (SEQ ID NO: 31), has been deposited on Dec. 11, 1996 with the American Type Culture Collection with Accession No. 98273. A Rac-GEF specific amino acid sequence means a defined amino acid sequence. A specific amino acid sequence can be found routinely, e.g., by searching a gene/protein database using the BLAST set of computer programs. A Rac-GEF specific amino acid sequence can be useful to produce peptides as antigens to generate an immune response specific for Rac-GEF. Antibodies obtained by such immunization can be used as a specific probe for the Rac-GEF protein for diagnostic or research purposes. Such peptides can also be used to inhibit the Rac-GEF binding to Rac to modulate pathological conditions in cells.

A polypeptide of the invention, e.g., having a polypeptide sequence as shown in FIG. 1 (SEQ ID NO: 2), can by analyzed by available methods to identify structural and/or functional domains in the polypeptide. For example, when the polypeptide coding sequence set forth in FIG. 1 (SEQ ID NO:2) is analyzed by computer algorithms, a continuous coding sequence comprising the following domains is identified: Src homology, Dbl homology and pleckstrin homology domains. Various programs can be employed to analyze structure of the polypeptide, including, EMBL Protein Predict; Rost and Sander, Proteins, 19:55–72, 1994; Kyte and Doolittle, J. Mol. Bio.: 157:105,1982.

A polypepfide of the present invention can also have 100% or less amino acid sequence identity to the amino acid sequence set forth in FIG. 1. (SEQ ID NO: 2). For the purposes of the following discussion: Sequence identity means that the same nucleotide or amino acid which is found in the sequence set forth in FIG. 1. (SEQ ID NO: 1 and SEQ ID NO: 2) is found at the corresponding position of the compared sequence(s). A polypeptide having less than 100% sequence identify to the amino acid sequence set forth in FIG. 1 (SEQ. ID NO: 2) can be substituted in various ways, e.g., by a conservative amino acid. See below for examples of conservative amino acid substitution. The sum of the identical and conserved residues divided by the total number of residues in the sequence over which the Rac-GEF polypeptide is compared is equal to the percent sequence similarity. For purposes of calculating sequence identity and similarity, the compared sequences can be aligned-and calculated according to any desired method, algorithm, computer program, etc., including, e.g., FASTA, BLASTA. A polypeptide having less than 100% amino acid sequence identity to the amino acid sequence of FIG. 1 (SEQ ID NO: 2) can comprise e.g., about 60, 65, more preferably, 67, 70, 78, 80, 90, 92, 96, 99, etc.

A Rac GEF polypeptide, fragment, or substituted GEF polypeptide can also comprise various modifications, where such modifications include glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

A mutation to a Rac-GEF polypeptide can be selected to have a biological activity of Rac-GEF, e.g., a specific binding affinity for a guanine nucleotide-depleted state of G-proteins, in particular Rac, a guanine nucleotide exchange activity, an oncogenic transforming activity, and an immunogenic activity. The selection and preparation of mutations of Rac-GEF is discussed below.

Polypeptides of the present invention (e.g., Rac-GEF, fragments thereto, mutations thereof) can be used in various ways, e.g., as immunogens for antibodies as described below, as biologically-active agents (e.g., having one or more of the activities associated with Rac-GEF), as inhibitors of Rac-GEF. For example, upon binding of Rac-GEF to Rac, a cascade of events is initiated in the cell, e.g., promoting cell proliferation and/or cytoskeletal rearrangements. The interaction between Rac-GEF and Rac can be modulated by using a peptide fragment of Rac-GEF, e.g., a peptide fragment which is an inhibitor at the site where Rac-GEF interacts (e.g., binds) to Rac. Such a fragment can be useful for modulating pathological conditions associated with the Rac signaling pathway. A useful fragment can be identified routinely by testing the ability of overlapping fragments of the entire length of Rac-GEF to inhibit a Rac-GEF activity, such as guanine nucleotide exchange activity, binding to a guanine nucleotide depleted state of Rac, and oncogenic transforming activity. The measurement of certain of these activities is described below, and in the examples. These peptides can also be identified and prepared as described in EP 496 162. Peptides can be chemically-modified, etc.

A polypeptide coding for a Rac-GEF polypeptide, or a derivative or fragment thereof, can be combined with one or more structural domains, functional domains, detectable domains, antigenic domains, and/or a desired polypeptides of interest, in an arrangement which does not occur in nature, i.e., not naturally-occurring, e.g., as in a normal Rac-GEF gene, a genomic fragment prepared from the genome of a living organism, e.g., an animal, preferably a mammal, such as human, mouse, or cell lines thereof. A polypeptide comprising such features is a chimeric or fusion polypeptide. Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as catalytic, signalling, growth promoting, cellular targeting, etc., a structural function such as hydrophobic, hydrophilic, membrane-spanning, etc., receptor-ligand functions, and/or detectable functions, e.g., combined with enzyme, fluorescent polypeptide, green fluorescent protein GFP (Chalfie et al., 1994, Science, 263:802; Cheng etal., 1996, Nature Biotechnology, 14:606; Levy et al., 1996, Nature Biotechnology, 14:610, etc. In addition, a Rac-GEF nucleic acid, or a part of it, can be used as selectable marker when introduced into a host cell. For example, a nucleic acid coding for an amino acid sequence according to the present invention can be fused in-frame to a desired coding sequence and act as a tag for purification, selection, or marking purposes. The region of fusion encodes a cleavage site.

A polypeptide according to the present invention can be produced in an expression system, e.g., in vivo, in vitro, cell-free, recombinant, cell fusion, etc., according to the present invention. Modifications to the polypeptide imparted by such system include, glycosylation, amino acid substitution (e.g., by differing codon usage), polypeptide processing such as digestion, cleavage, endopeptidase or exopeptidase activity, attachment of chemical moieties, including lipids, phosphates, etc. For example, some cell lines can remove the terminal methionine from an expressed polypeptide.

A polypeptide according to the present invention can be recovered from natural sources, transformed host cells (culture medium or cells) according to the usual methods, including, ammonium sulfate or ethanol precipitation, acid extraction, anion or cation exchange chromatography, phosphocellulose chromatography, hydrophobic interaction chromatography, hydroxyapatite chromatography and lectin chromatography. It may be useful to have low concentrations (approximately 0.1–5 mM) of calcium ion present during purification (Price, et al., *J. Biol. Chem.*, 244:917 (1969)). Protein refolding steps can be used, as necessary, in completing the configuration of the mature protein. Finally, high performance liquid chromatography (HPLC) can be employed for final purification steps.

In accordance with the present invention, a nucleic acid coding for a Rac-GEF can comprise, e.g., the complete coding sequence as set forth in FIG. 1 (SEQ ID NO: 1). A nucleic acid according to the present invention can also comprise a nucleotide sequence which is 100% complementary, e.g., an anti-sense, to any nucleotide sequence mentioned above and below.

A Rac GEF encoding nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell at a particular stage of development, having a desired genotype, phenotype (e.g., an oncogenically transformed cell or a cancerous cell), etc.

A nucleic acid comprising a nucleotide sequence coding for a polypeptide according to the present invention can include only coding sequence of Rac-GEF; coding sequence of Rac-GEF and additional coding sequence (e.g., sequences coding for leader, secretory, targeting, enzymatic, fluorescent or other diagnostic peptides), coding sequence of Rac-GEF and non-coding sequences, e.g., untranslated sequences at either a 5' or 3' end, or dispersed in the coding sequence, e.g., introns. A nucleic acid comprising a nucleotide sequence coding without interruption for a Rac-GEF polypeptide means that the nucleotide sequence contains an amino acid coding sequence for a Rac-GEF polypeptide, with no non-coding nucleotides interrupting or intervening in the coding sequence, e.g., absent intron(s). Such a nucleotide sequence can also be described as contiguous.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids which hybridize to a nucleic acid comprising a nucleotide sequence as set forth in FIG. 1 (SEQ ID NO: 1). A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIG. 1 (SEQ ID NO: 1). A nucleic acid capable of hybridizing to such sequence, preferably, possesses 50%, more preferably, 70% complementarity, between the sequences. The present invention particularly relates to DNA sequences which hybridize to the nucleotide sequence set forth in FIG. 1 (SEQ ID NO: 1) under stringent conditions. As used here, "stringent conditions" means any conditions in which hybridization will occur where there is at least about 95%, preferably 97%, nucleotide complementarity between the nucleic acids. Such conditions include, e.g., hybridization for Northern: 5× SSPE, 10× Denhardts solution, 100 µg/ml freshly denatured and sheared salmon sperm DNA, 50% formamide, 2% SDS at 42° C.; hybridization for cloning from cDNA library: 1× PAM, 0.1% SDS, 50% formamide at 42° C.

According to the present invention, a nucleic acid or polypeptide can comprise one or more differences in the nucleotide or amino acid sequence set forth in FIG. 1 (SEQ ID NO: 1 and SEQ ID NO: 2). Changes or modifications to the nucleotide and/or amino acid sequence can be accomplished by any method available, including directed or random mutagenesis.

A nucleic acid coding for a Rac-GEF according to the invention can comprise nucleotides which occur in a naturally-occurring Rac-GEF gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtained from a natural source, e.g., animal tissue and cells, body fluids, tissue culture cells, forensic samples. Naturally-occurring mutations to Rac-GEF can include deletions (e.g., a truncated amino- or carboxy-terminus), substitutions, or additions of nucleotide sequence. These genes can be detected and isolated by nucleic acid hybridization according to methods which one skilled in the art would know. It is recognized that, in analogy to other oncogenes, naturally-occurring variants of Rac-GEF include deletions, substitutions, and additions which produce pathological conditions in the host cell and organism.

A nucleotide sequence coding for a Rac-GEF polypeptide of the invention can contain codons found in a naturally-occurring gene, transcript, or cDNA, for example, e.g., as set forth in FIG. 1 (SEQ ID NO: 1), or it can contain degenerate codons coding for the same amino acid sequences.

In addition, a nucleic acid or polypeptide of the present invention can be obtained from any desired mammalian organism, but also non-mammalian organisms. Homologs from mammalian and non-mammalian organisms can be obtained according to various methods. For example, hybridization with an appropriate oligonucleotide selective for Rac-GEF can be employed to select such homologs, e.g., as described in Sambrook et al., *Molecular Cloning,* 1989, Chapter 11.

Such homologs can have varying amounts of nucleotide and amino acid sequence identity and similarity to Rac-GEF. Non-mammalian organisms include, e.g., vertebrates, invertebrates, chicken, Drosophila, yeasts (such as *Saccharomyces cerevisiae*), *C. elegans,* roundworms, prokaryotes, plants, Arabidopsis, viruses, etc.

Modifications to a Rac-GEF sequence, e.g., mutations, can also be prepared based on homology searching from gene data banks, e.g., Genbank, EMBL. Sequence homology searching can be accomplished using various methods, including algorithms described in the BLAST family of computer programs, the Smith-Waterman algorithm, etc. For example, conserved amino acids can be identified between various sequences, Dbl, lbc, Ost, lsc, CDC24, etc. See, e.g., Touhara et al., *J. Biol. Chem.,* 269:10217–10220, 1994; Toksoz and Williams, Oncogene, 9:621–628, 1994; Whitehead et al., *J. Biol. Chem.,* 271:18643–18650, 1996. A mutation(s) can then be introduced into a Rac-GEF sequence by identifying and aligning amino acids conserved between the polypeptides and then modifying an amino acid in a conserved or non-conserved position. A mutated Rac-GEF gene can comprise conserved or nonconserved amino acids, e.g., between corresponding regions of homologous nucleic acids, especially between Dbl homology (DH) domains, etc. For example, a mutated sequence can comprise conserved or non-conserved residues from any number of homologous sequences as mentioned-above and/or determined from an appropriate searching algorithm.

Mutations can be made in specific regions of nucleic acid coding for the Rac-GEF polypeptide, e.g., in the Dbl homology domain, such as replacing it, changing amino acid sequences within it, etc., to analyze a function (e.g., oncogenic transformation, binding to a G-protein, guanine nucleotide exchange) of the polypeptide coded for by the nucleic acid. For example, deletion of the pleckstrin domain would result in the loss of oncogenic transforming activity. The pleckstrin domain can also be involved with lipid (e.g., phosphoinositides) binding, binding to Rac, activation of the guanine nucleotide exchange activity, and localization of the polypeptide in the cell. Thus, this region can be mutagenized according to various methods and then assayed for loss or gain of the mentioned functions. The DH domain is involved with promoting GDP dissociation from the Rac GTPase. Thus, substitutions or deletions within this region can be prepared and assayed routinely for loss or gain of function. A mutation can be made in these or other regions of Rac-GEF which affect its phosphorylation or protein/lipid interaction leading to its modulation of the growth signaling pathway. Such a mutated gene can be useful in various ways: for diagnosis in patients having such a mutation, to introduce into cells or animals (transgenic) as a model for a pathological condition. Mutations which affect both GEF activity and transforming activity can be analogous to those made in the DH domain of the Dbl oncogene as described in Hart et al., *J. Biol. Chem.,* 269:62–65.

A nucleic acid and corresponding polypeptide of the present invention include sequences which differ from the nucleotide sequence of FIG. 1 (SEQ ID NO: 1) but which are phenotypically silent. These sequence modifications include, e.g., nucleotide substitution which do not affect the amino acid sequence (e.g., different codons for the same amino acid), replacing naturally-occurring amino acids with homologous or conservative amino acids, e.g., (based on the size of the side chain and degree of polarization) small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine. Such conservative substitutions also include those described by Dayhoff in the *Atlas of Protein Sequence and Structure* 5 (1978), and by Argos in *EMBO J.,* 8 779–785 (1989).

A nucleic acid can comprise a nucleotide sequence coding for a polypeptide having an amino acid sequence as set forth in FIG. 1. (SEQ ID NO: 2) except where one or more positions are substituted by conservative amino acids; or a nucleotide sequence coding for a polypeptide having an amino acid sequence as set forth in FIG. 1. (SEQ ID NO:2). The invention also relates to polypeptides coded for by such nucleic acids. In addition, it may be desired to change the codons in the sequence to optimize the sequence for expression in a desired host.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNase H, improved in vivo stability, etc. See, e.g., U.S. Pat. No. 5,378,825.

Various modifications can be made to the nucleic acids, such as attaching detectable markers (avidin, biotin, radioactive elements), moieties which improve hybridization, detection, or stability. The nucleic acids can also be attached to solid supports, e.g., nitrocellulose, nylon, agarose, diazotized cellulose, latex solid microspheres, polyacrylamides, etc., according to a desired method. See, e.g., U.S. Pat. Nos. 5,470,967, 5,476,925, 5,478,893.

Another aspect of the present invention relates to oligonucleotides and nucleic acid probes. Such oligonucleotides or nucleic acid probes can be used, e.g., to detect, quantitate, or isolate a Rac-GEF nucleic acid in a test sample. Detection can be desirable for a variety of different purposes, including research, diagnostic, and forensic. For diagnostic purposes, it may be desirable to identify the presence or quantity of a Rac-GEF nucleic acid sequence in a sample, where the sample is obtained from tissue, cells, body fluids, etc. In a preferred method, the present invention relates to a method of detecting a Rac-GEF nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR, e.g., Saiki et al., 1988, Science, 241:53; U.S. Pat. No. 4,683,202.

Another aspect of the present invention is a nucleotide sequence which is unique to Rac-GEF. By a unique sequence to Rac-GEF, it is meant a defined order of nucleotides which occurs in Rac-GEF, e.g., in the nucleotide sequence of FIG. 1 (SEQ ID NO: 1), but rarely or infrequently in other nucleic acids, especially not in an animal nucleic acid, preferably mammal, such as human, rat, mouse, etc. Both sense and antisense nucleotide sequences are included. A unique nucleic acid according to the present invention can be determined routinely. A nucleic acid comprising a unique sequence of Rac-GEF can be used as a hybridization probe to identify the presence of Rac-GEF in a sample comprising a mixture of nucleic acids, e.g., on a Northern blot. Hybridization can be performed under stringent conditions to select nucleic acids having at least 95% identity (i.e., complementarity) to the probe, but less stringent conditions can also be used. A unique Rac-GEF nucleotide sequence can also be fused in-frame, at either its 5' or 3' end, to various nucleotide sequences as mentioned throughout the patent, including coding sequences for other parts of Rac-GEF, enzymes, GFP, etc, expression control sequences, etc.

Hybridization can be performed under different conditions, depending on the desired selectivity, e.g., as described in Sambrook et al., *Molecular Cloning*, 1989. For example, to specifically detect Rac-GEF, an oligonucleotide can be hybridized to a target nucleic acid under conditions in which the oligonucleotide only hybridizes to Rac-GEF, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%. Since a mutation in a Rac-GEF gene can cause diseases or pathological conditions, e.g., cancer, benign tumors, an oligonucleotide according to the present invention can be used diagnostically. For example, a patient having symptoms of a cancer or other condition associated with the Rac signaling pathway (see below) can be diagnosed with the disease by using an oligonucleotide according to the present invention, in polymerase chain reaction followed by DNA sequencing to identify whether the sequence is normal, in combination with other oncogene oligonucleotides, etc., e.g., p53, Rb, p21, Dbl, MTS1, Wt1, Bcl-1, Bcl-2, MDM2, etc. In a preferred method, the present invention relates to a method of diagnosing a cancer comprising contacting a sample comprising a target nucleic acid with an oligonucleotide under conditions effective to permit hybridization between the target and oligonucleotide; detecting hybridization, wherein the oligonucleotide comprises a sequence of Rac-GEF, preferably a unique sequence of Rac-GEF; and determining the nucleotide sequence of the target nucleic acid to which the oligonucleotide is hybridized. The sequence can be determined according to various methods, including isolating the target nucleic acid, or a cDNA thereof, and determining its sequence according to a desired method.

Oligonucleotides according to the present invention can be of any desired size, preferably 14–16 oligonucleotides in length, or more. Such oligonucleotides can have non-naturally-occurring nucleotides, e.g., inosine. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Anti-sense nucleic acid can also be prepared from a nucleic acid according to the present, preferably an anti-sense to a coding sequence of FIG. 1 (SEQ ID NO: 1). Antisense nucleic acid can be used in various ways, such as to regulate or modulate expression of Rac-GEF, e.g., inhibit it, to detect its expression, or for in situ hybridization. For the purposes of regulating or modulating expression of Rac-GEF, an anti-sense oligonucleotide can be operably linked to an expression control sequence.

The nucleic acid according to the present invention can be labelled according to any desired method. The nucleic acid can be labeled using radioactive tracers such as $^{32}P$, $^{35}S$, $^{125}I$, $^{3}H$, or $^{14}C$, to mention only the most commonly used tracers. The radioactive labelling can be carried out according to any method such as, for example, terminal labeling at the 3' or 5' end using a radiolabeled nucleotide, polynucleotide kinase (with or without dephosphorylation with a phosphatase) or a ligase (depending on the end to be labelled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligonucleotides, anti-sense nucleic acid, etc., can be used to detect expression of Rac-GEF in whole organs, tissues, cells, etc., by various techniques, including Northern blot, PCR, in situ hybridization, etc. Such nucleic acids can be particularly useful to detect disturbed expression, e.g., cell-specific and/or subcellular alterations, of Rac-GEF. The levels of Rac-GEF can be determined alone or in combination with other genes products (oncogenes such as p53, Rb, Wt1, etc.), transcripts, etc.

A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for the nucleic acid. Effective conditions includes any culture conditions which are suitable for achieving production of the polypeptide by the host cell, including effective temperatures, pH, medias, additives to the media in which the host cell is cultured (e.g., additives which amplify or induce expression such as butyrate, or methotrexate if the coding nucleic acid is adjacent to a dhfr gene), cyclohexamide, cell densities, culture dishes, etc. A nucleic acid can be introduced into the cell by any effective method including, e.g., calcium phosphate precipitation, electroporation, injection, DEAE-Dextran mediated transfection, fusion with liposomes, and viral transfection. A cell into which a nucleic acid of the present invention has been introduced is a transformed host cell. The nucleic acid can be extrachromosomal or integrated into a chromosome (s) of the host cell. It can be stable or transient. An expression vector is selected for its compatibility with the host cell. Host cells include, mammalian cells, e.g., COS-7, CHO, HeLa, LTK, NIH 3T3, Rat 1 fibroblasts, yeast, insect cells, such as Sf9 (*S. frugipeda*) and Drosophila, bacteria, such as *E. coli*, Streptococcus, bacillus, yeast, fungal cells, plants, embryonic stem cells (e.g., mammalian, such as mouse or human), cancer or tumor cells. Sf9 expression can be accomplished in analogy to Graziani et al., *Oncogene*, 7:229–235, 1992. Expression control sequences are similarly selected for host compatibility and a desired purpose, e.g., high copy number, high amounts, induction, amplification, controlled expression. Other sequences which can be employed include enhancers such as from SV40, CMV, inducible promoters, cell-type specific elements, or sequences which allow selective or specific cell expression.

In addition to a Rac-GEF nucleic acid, another gene of interest can be introduced into the same host for purposes of, e.g., modulating expression Rac-GEF, elucidating Rac-GEF function or that of the gene of interest. Genes of interest include other oncogenes, genes involved in the cell cycle, etc. Such genes can be the normal gene, or a variation, e.g., a mutation, chimera, polymorphism, etc.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. For example, the Rac-GEF polypeptide from fetal brain can also be used as a molecular weight marker of about 74.7 kDa for a protein gel.

Another aspect of the present invention relates to the regulation of biological pathways in which a GTPase is involved, particularly pathological conditions, e.g., cell proliferation (e.g., cancer), growth control, morphogenesis, stress fiber formation, and integrin-mediated interactions, such as embryonic development, tumor cell growth and metastasis, programmed cell death, hemostasis, leucocyte homing and activation, bone resorption, clot retraction, and the response of cells to mechanical stress. See, e.g., Clark and Brugge, Science, 268:233–239, 1995; Bussey, Science, 272:225–226, 1996. Thus, the invention relates to all aspects of a method of modulating an activity of a Rac polypeptide comprising, administering an effective amount of a Rac-GEF polypeptide or a biologically-active fragment thereof, an effective amount of a compound which modulates the activity of a Rac polypeptide, or an effective amount of a nucleic acid which codes for a Rac-GEF polypeptide or a biologically-active fragment thereof. The activity of Rac which is modulated can include: GTP binding, GDP binding, GTIase activity, integrin binding, coupling or binding of Rac to receptor or effector-like molecules (such as integrins, growth factor receptors, tyrosine kinases, PI-3K, PIP-5K, etc.). See, e.g., Clark and Brugge, Science, 268:233–239, 1995. The activity can be modulated by increasing, reducing, antagonizing, promoting, etc. of Rac. The modulation of Rac can be measured by assay for GTP hydrolysis, binding to Rac-GEF, etc. An effective amount is any amount which, when administered, modulates the Rac activity. The activity can be modulated in a cell, a tissue, a whole organism, in situ, in vitro (test tube, a solid support, etc.), in vivo, or in any desired environment.

Compounds that regulate the interaction between a GEF, such Rac-GEF, and a GTPase can be identified using an assay for a GEF activity, such as guanine nucleotide exchange activity, binding to a guanine nucleotide-depleted site of a GTPase, or oncogenic transforming activity, or a GTPase activity such as GTP hydrolysis. In general, a compound having such an in vitro activity will be useful in vivo to modulate a biological pathway associated with a GTPase, e.g., to treat a pathological condition associated with the biological and cellular activities mentioned above. By way of illustration, the ways in which GEF regulators can be identified are described above and below in terms of Rac and Rac-GEF. However, it is to be understood that such methods can be applied generally to other GEFs.

A guanine nucleotide exchange assay, e.g., as described in Hart et al., *Nature*, 354:311–314, 28 Nov. 1991 (see, especially, FIG. 2 legend therein), can be used to assay for the ability of a compound to regulate the interaction between Rac and Rac-GEF. For example, Rac protein (recombinant, recombinant fusion protein, or isolated from natural sources) is labeled with tritiated-GDP. The tritiated-GDP-labeled Rac is then incubated with Rac-GEF and GTP under conditions in which nucleotide exchange occurs. The amount of tritiated-GDP that is retained by Rac is determined by separating bound GDP from free GDP, e.g., using a BA85 filter. The ability of a compound to regulate the interaction can be determined by adding the compound at a desired time to the incubation (e.g., before addition of a Rac-GEF, after addition of a Rac-GEF) and determining its effect on nucleotide exchange. Various agonist and antagonists of the interaction can be identified in this manner. For instance, an aspect of the instant invention is the discovery that certain compounds greatly enhance the activity of Rac-GEFs, and preferrably of the Rac-GEF, Tiam-1. Such compounds are hereinafter termed "GEF enhancers." Such compounds have certain similar chemical features including a hydrocarbon arm, preferrably consisting of substantially saturated bonds that link the carbon residues together, and also preferrably the number of carbon atoms should be between 12–22. A second feature of such compounds is the association of the hydrocarbon arm to either a 5 or 6 membered ring structure. Preferred 5 or 6 membered compounds include ascorbate and certain cyclohexanes, respectively. The more preferred 5 membered compounds are derivatives of ascorbate, while the more preferred cyclohexanes include insoitol.

Binding to a guanine nucleotide-depleted site of Rac can be determined in various ways, e.g., as described in Hart et al., J. Biol. Chem., 269:62–65, 1994. Briefly, a Rac protein can be coupled to a solid support using various methods that one skilled in the art would know, e.g., using an antibody to Rac, a fusion protein between Rac and a marker protein, such as glutathione protein (GST), wherein the fusion is coupled to a solid support via the marker protein (such as glutathionine beads when GST is used), etc. The Rac protein is converted to a guanine nucleotide depleted state (for effective conditions, see, e.g., Hart et al., J. Biol. Chem., 269:62–65, 1994) and incubated with, e.g., GDP, GTPγS, and a GEF such as Rac-GEF. The solid support is then separated and any protein on it run on a gel. A compound can be added at any time during the incubation (as described above) to determine its effect on the binding of the GEF to Rac.

The modulation of oncogenic transforming activity by a Rac-GEF, or derivatives thereof, can be measured according to various known procedures, e.g., Eva and Aaronson, Nature, 316:273–275, 1985; Hart et al., J. Biol. Chem., 269:62–65,1994. A compound can be added at any time during the method (e.g., pretreatment of cells; after addition of GEF, etc.) to determine its effect on the oncogenic transforming activity of Rac-GEF. Various cell lines can also be used.

Other assays for Rac-mediated signal transduction can be accomplished according to procedures known in the art, e.g., as described in U.S. Pat. Nos. 5,141,851; 5,420,334; 5,436, 128; and 5,482,954; WO94/16069; WO93/16179; WO91/15582; WO90/00607. In addition, peptides which inhibit the interaction, e.g., binding, between Rac-GEF and a G-protein, such as Rac, can be identified and prepared according to EP 496 162.

The present invention also relates to a method of testing for and identifying an agent which modulates the guanine nucleotide exchange activity of a guanine nucleotide exchange factor, or a biologically-active fragment thereof, or which modulates the binding between a Rac-GEF, or a biologically-active fragment thereof, and a GTPase, or a biologically-active fragment thereof, to which it binds. The method comprises contacting the GEF and GTPase with an agent to be tested and then detecting the presence or amount of binding between the GEF and GTPase, or an activity of the GEF such as guanine nucleotide exchange activity. By modulating, it is meant that addition of the agent affects the activity or binding. The binding or activity modulation can be affected in various ways, including inhibiting, blocking, preventing, increasing, enhancing, or promoting it. The binding or activity affect does not have to be achieved in a specific way, e.g., it can be competitive, noncompetitive, allosteric, sterically hindered, via cross-linking between the agent and the GEF or GTPase, etc. The agent can act on either the GEF or GTPase. The agent can be an agonist, an antagonist, or a partial agonist or antagonist. The presence or amount of binding can be determined in various ways, e.g., directly or indirectly by assaying for an activity promoted or inhibited by the GEF, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof. See, e.g., Hoeprich, *Nature Biotechnology,* 14:1311–1312,1996, which describes an example of automated synthesis of organic molecules. The agent can be added simultaneously or sequentially. For example, the agent can be added to the GEF and then the resultant mixture can be further combined with the GTPase. The method can be carried out in liquid on isolated components, on a matrix (e.g., filter paper, nitrocellulose, agarose), in cells, on tissue sections, etc. In accordance with the method, a GEF can bind to the GTPase, which binding will modulate some GTPase activity. For example, as discussed above and below, a Rac-GEF binds to Rac, causing guanine nucleotide dissociation. The effect can be directly on the binding site between the GEF and GTPase, or it can be allosteric, or it can be on only one component (e.g., on the GEF only). Assays for guanine nucleotide dissociation can be readily adapted to identify agents which regulate the activity of a GTPase. The method further relates to obtaining or producing agents which have been identified according to the above-described method.

The present invention also relates to products identified in accordance with such methods. Various GEFs and GTPases can be employed, including, -Rac-GEF, mSOS, SOS, C3G, lsc, Dbl, Dbl-related proteins, polypeptides comprising one or more DH domains, CDC24, Tiam-1, Ost, Lbc, Vav, Ect2, Bcr, Abr, Rho (A, B, and C), Rac, Ras, CDC42, chimeras thereof, biologically-active fragments thereof, muteins thereof, etc.

The present invention thus also relates to the treatment and prevention of diseases and pathological conditions associated with Rac-mediated signal transduction, e.g., cancer, diseases associated with abnormal cell proliferation. For example, the invention relates to a method of treating cancer comprising administering, to a subject in need of treatment, an amount of a compound effective to treat the disease, where the compound is a regulator of Rac-GEF gene or polypeptide expression. Treating the disease can mean, delaying its onset, delaying the progression of the disease, improving or delaying clinical and pathological signs of disease. Similarly, the method also relates to treating diseases associated with inflammation, and/or the chemotactic ability of neutrophils. A regulator compound, or mixture of compounds, can be synthetic, naturally-occurring, or a combination. A regulator compound can comprise amino acids, nucleotides, hydrocarbons, lipids, polysaccharides, etc. A regulator compound is preferably a regulator of Rac-GEF, e.g., inhibiting or increasing its mRNA, protein expression, or processing, or its interaction with Rac, e.g., guanine nucleotide exchange. Additionally, cells can be supplemented with Rac-GEF, or derivatives thereof. To treat the disease, the compound, or mixture, can be formulated into pharmaceutical composition comprising a pharmaceutically acceptable carrier and other excipients as apparent to the skilled worker. See, e.g., *Remington's Pharmaceutical Sciences,* Eighteenth Edition, Mack Publishing Company, 1990. Such composition can additionally contain effective amounts of other compounds, especially for treatment of cancer.

The present invention also relates to antibodies which specifically recognize a Rac-GEF polypeptide. Antibodies, e.g., polyclonal, monoclonal, recombinant, chimeric, can be prepared according to any desired method. For example, for the production of monoclonal antibodies, a polypeptide according to FIG. 1 (SEQ ID NO: 2), can be administered to mice, goats, or rabbit subcutaneously and/or intraperitoneally, with or without adjuvant, in an amount effective to elicit an immune response. The antibodies can also be single chain or FAb. The antibodies can be IgG, subtypes, IgG2a, IgG1, etc.

An antibody specific for Rac-GEF means that the antibody recognizes a defined sequence of amino acids within or including the Rac-GEF amino acid sequence of FIG. 1 (SEQ ID NO: 2). Thus, a specific antibody will bind with higher affinity to an amino acid sequence, i.e., an epitope, found in FIG. 1 (SEQ ID NO: 2) than to a different epitope(s), e.g., as detected and/or measured by an immunoblot assay. Thus, an antibody which is specific for an epitope of Rac-GEF is useful to detect the presence of the epitope in a sample, e.g., a sample of tissue containing Rac-GEF gene product, distinguishing it from samples in which the epitope is absent. Such antibodies are useful as described in Santa Cruz Biotechnology, Inc., Research Product Catalog, can be formulated accordingly, e.g., 100 μg/ml.

In addition, ligands which bind to a Rac-GEF polypeptide according to the present invention, or a derivative thereof, can also be prepared, e.g., using synthetic peptide libraries, or nucleic acid ligands (e.g., Pitrung et al., U.S. Pat. No. 5,143,854; Geysen et al., 1987, J. Immunol. Methods, 102:259–274; Scott et al., 1990, Science, 249:386; Blackwell et al., 1990, Science, 250:1104; Tuerk et al., 1990, Science, 249: 505.

Antibodies and other ligands which bind Rac-GEF can be used in various ways, including as therapeutic, diagnostic, and commercial research tools, e.g, to quantitate the levels of Rac-GEF polypeptide in animals, tissues, cells, etc., to identify the cellular localization and/or distribution of Rac-GEF, to purify Rac-GEF or a polypeptide comprising a part of Rac-GEF, to modulate the function of Rac-GEF, etc. Antibodies to Rac-GEF, or a derivative thereof, can be used in Western blots, ELISA, mmunoprecipitation, RIA, etc. The present invention relates to such assays, compositions and kits for performing them, etc.

An antibody according to the present invention can be used to detect Rac-GEF polypeptide or fragments thereof in various samples, including tissue, cells, body fluid, blood, urine, cerebrospinal fluid. A method of the present invention comprises contacting a ligand which binds to a peptide of FIG. 1. (SEQ ID NO: 2) under conditions effective, as known in the art, to achieve binding, detecting specific binding between the ligand and peptide. By specific binding, it is meant that the ligand attaches to a defined sequence of amino acids, e.g., within or including the amino acid sequence of FIG. 1. (SEQ ID NO: 2) or derivatives thereof.

The antibodies or derivatives thereof can also be used to inhibit expression of Rac-GEF or a fragment thereof. The levels of Rac-GEF polypeptide can be determined alone or in combination with other gene products. In particular, the amount (e.g., its expression level) of Rac-GEF polypeptide can be compared (e.g., as a ratio) to the amounts of other polypeptides in the same or different sample, e.g., p21, p53, Rb, WT1, etc.

A ligand for Rac-GEF can be used in combination with other antibodies, e.g., antibodies that recognize oncological markers of cancer, including, Rb, p53, c-erbB-2, oncogene products, etc. In general, reagents which are specific for Rac-GEF can be used in diagnostic and/or forensic studies according to any desired method, e.g., as U.S. Pat. Nos. 5,397,712; 5,434,050; 5,429,947.

The present invention also relates to a labelled Rac-GEF polypeptide, prepared according to a desired method, e.g., as disclosed in U.S. Pat. No. 5,434,050. A labelled polypeptide can be used, e.g., in binding assays, such as to identify substances that bind or attach to Rac-GEF, to track the movement of Rac-GEF in a cell, in an in vitro, in vivo, or in situ system, etc.

A nucleic acid, polypeptide, antibody, Rac-GEF ligand etc., according to the present invention can be isolated. The term "isolated" means that the material is in a form in which it is not found in its original environment, e.g., more concentrated, more purified, separated from component, etc. An isolated nucleic acid includes, e.g., a nucleic acid having the sequence of Rac-GEF separated from the chromosomal DNA found in a living animal. This nucleic acid can be part of a vector or inserted into a chromosome (by specific gene-targeting or by random integration at a position other than its normal position) and still be isolated in that it is not in a form which is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a Rac-GEF nucleic acid. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al., *Proc. Natl. Acad. Sci.*, 77:7380–7384 (1980); Palmiter et al., *Cell*, 41:343–345 (1985); Palmiter et al., *Ann. Rev. Genet.*, 20:465–499 (1986); Askew et al., *Mol. Cell. Bio.*, 13:4115–4124, 1993; Games et al. *Nature*, 373:523–527, 1995; Valancius and Smithies, *Mol. Cell. Bio.*, 11:1402–1408, 1991; Stacey et al., *Mol. Cell. Bio.*, 14:1009–1016, 1994; Hasty et al., *Nature*, 350:243–246, 1995; Rubinstein et al., *Nucl. Acid Res.*, 21:2613–2617, 1993. A nucleic acid according to the present invention can be introduced into any non-human mammal, including a mouse (Hogan et al., 1986, in *Manipulating the Mouse Embryo: A Laboratory Manual*, Cold Spring Harbor Laboratory, Cold Spring Harbor, N.Y.), pig (Hammer et al., *Nature*, 315:343–345, 1985), sheep (Hammer et al., *Nature*, 315:343–345, 1985), cattle, rat, or primate. See also, e.g., Church, 1987, *Trends in Biotech.* 5:13–19; Clark et al., 1987, *Trends in Biotech.* 5:20–24; and DePamphilis et al., 1988, *BioTechniques*, 6:662–680. In addition, e.g., custom transgenic rat and mouse production is commercially available. These transgenic animals are useful as a cancer model, e.g., to test drugs.

Generally, the nucleic acids, polypeptides, antibodies, etc. of the present invention can be prepared and used as described in U.S. Pat. Nos. 5,501,969; 5,506,133; 5,441,870; WO 90/00607; and WO 91/15582.

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevir Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science;* Edited by John E. Coligan et al., John Wiley & Sons, Inc.; *Current Protocols in Immunology;* Edited by John E. Coligan et al., John Wiley & Sons, Inc.

EXAMPLES

Example 1

Cloning of cDNA Encoding Rac GEF

A Dbl-homology domain containing protein was identified in a human fetal brain cDNA library as follows. A TBLASTN search of the dbEST database was performed using the amino acid sequence (residues 1–519) encoded by the human TIM protein (Chan et al., 1994, Oncogene, Vol. 9, pages 1057–1063). One EST clone, #167059 was identified with high sequence homology to the TIM cDNA. The plasmid encoding this insert was purchased via the I.M.A.G.E. Consortium (Research Genetics). Using this cDNA as template, a 511-bp $^{32}$P-labelled PCR product was produced using oligos 5'-GGAGGCCATGTTCGAGCTGG-3' SEQ ID NO.3 and 5'-GCTGATCATCTGTTCCGTGC-3' SEQ ID NO.4 (5' and 3' primers, respectively) and $^{32}$P labelled nucleotides. This labeled PCR fragment was used as a probe to screen approximately 4×10$^5$ clones of a human fetal brain Lambda ZAP cDNA library (Stratagene). A clone with an insert of 2.6-kb was isolated, and the complete DNA sequence of this clone was determined using an ABI sequencer. This 2.6-kb clone harbored a single open reading frame of 1950-bp that is predicted to encode a 650-amino acids protein with a calculated molecular mass of 74.7 kDa. However, this open reading frame is not full-length, as the initiating methionine is missing. This cDNA is on deposit with the American Type Culture Collection, Dec. 11, 1996, with the Accession No.98273, and is denoted p67 Rac-GEF.

Northern analysis using the probe described above was conducted. The results revealed a 3.5 kb transcript specific to brain tissue and an additional 4 kb transcript of lower abundance specific to liver tissue. Other normal tissues tested, including heart, placenta, lung, muscle, kidney, pancreas, spleen, thymus, prostate, testis, ovary, intestine, colon and peripheral blood lymphocytes were also essentially negative. In a preliminary screen of human tumor cell lines, abundant 3.5 kb mRNA levels were detected in the lung carcinoma cell line A549 and the colon carcinoma cell line SW480. Other tumor cell lines were negative, including HL-60, HeLa, K-562, Molt-4, Raji and G-36. Further screening of a number of primary tumor samples revealed over-expression in liver, lung and colon tumors.

Using the additional sequence identified in the 2.6-kb clone, further analysis of the dbEST database using the Blastn program identified an additional clone, #109922, which had been isolated from a liver library. The plasmid encoding this insert was purchased via the I.M.A.G.E. Consortium (Genome Systems), and the sequence of the insert was determined. This sequence revealed an initiating methionine and 126 additional amino acids which differed from the amino-terminal 66 amino acids of the 2.6 kb brain clone described above. This new sequence most likely encodes the liver-specific alternatively spliced form which had been identified by Northern analysis. Pieced together with the previously determined sequence, this liver-derived sequence reveals an open reading frame of 2133-bp predicted to encode a 710-amino acid protein.

In addition to the alternatively-spliced brain/liver isoforms, another putative splice variant was identified: an insertion of 72-bp coding for 24-amino acids within the Dbl homology region is encoded by the 2.6-kb brain clone. The sequence encoded by these 24-amino acids is conserved among other exchange factors including Tim (Chan et al., 1994, Oncogene, Vol. 9, pages 1057–1063) and Vav2 (Henske et al., 1995, Ann Hum Genet 59, Pt. 1, pages 25–37).

Example 2

Properties of Rac GEF

Two Rac-GEFs were tested for guanine nucleotide activity. Firstly, a Glu-epitope tag (MEYMPMEIRHD) (SEQ ID NO:32) was engineered onto the carboxy-terminal 423 amino acids of the Rac GEF encoded by EST No. 167059 by introducing the oligos 5'-TCGAGGAGGTTATAAATATGGAATACATGCCAAT GGA-3' SEQ ID NO.5 and the complementary 5'-AATTTCCATTGGCATGTATTCCATATTTATAACCTCC-3' SEQ ID NO.6 into the XhoI/EcoRI sites of the clone. The protein encoded by this construct is referred to as Type I Rac-GEF.

Next, the sequence encoding the insertion in the Dbl homology region, as described in Example 1, was engineered into the open reading frame in the expression plasmid pET21a (Novagen). The protein encoded by this construct is referred to as Type II Rac-GEF. The resulting expression plasmids were introduced into E. coli strain BL21(DE3) pLysS (Novagen), and the epitope tagged protein expression was induced with IPTG. The expressed proteins were purified using a resin with the antibody to the Glu-epitope covalently attached. The resulting proteins were partially pure and were assayed for exchange activity on Rac1, RhoA and Cdc42. See, Hart, in U.S. Ser. No. 60/029,979, filed Nov. 6, 1996 now abandoned. The results showed that Rac GEF is primarily selective for Rac1, but also displays activity against both RhoA and Cdc42. Furthermore, the Type I form lacking the Dbl insert region is unaffected by the addition of the PH domain ligand ascorbyl stearate, while the Type II form containing the Dbl insert region is strongly stimulated by ascorbyl stearate.

Example 3

Immunochemical Detection

Antibody specific to Rac-GEF was raised in rabbits against three fragments of the purified recombinant molecule. The fragments correspond to amino acids 385–398, Type II and amino acids, 372–386 of Type I Rac-GEF referred to in Example 2, and 693–710 amino acids of Type II. The peptides were coupled to KLH, and antibody raised in rabbits using standard procedures.

Example 4

Cloning and Expression of Tiam-1 and Truncations Thereof

Cloning and expression of Tiam-1, and various Tiam-1 truncations, is described below. This work, and that shown in Examples 5 and 6, was undertaken to determine those regions of Tiam-1 that realize GEF enhancer stimulation of Rac GEF activity.

cDNA Cloning Of Human Tiam-1 and Tiam-1 Truncations: Primers designed against published mouse Tiam-1 cDNA sequence (See, Habets, G. G, Scholtes, E. H., Zuydgeest, D., van der Kammen, R. A., Stam, J. C., Berns, A., and Collard, J. G. (1994) Cell 77,537–549; NCBI Gen Bank Accession #U05245) were used in PCR reactions using a human fetal brain library (Stratagene #936206) as template to obtain fragments of the human Tiam-1 gene which were radiolabled and used as probes in Southern hybridizations of the same library. Primer pairs used were both 5'-CCATAAAACCATGGGAAACGC-3' SEQ ID NO.7 and 5'-GGTTCCGCGGAAGAGAAGGAT-3' SEQ ID NO.8 with 5'-GACTGGCCCGGGGAACTGAGG-3' SEQ ID NO.9; and 5'-TCGGATGCGGATAAGCTGCGC-3' SEQ ID NO.10 with 5'-GTGACTGGCGACCTTGTTCAT-3' SEQ ID NO.11. Two partial clones of human Tiam-1 cDNA were retrieved, one contained nucleotides (nt) 1–2972 and the other (nt) 2972–4657 (numbering throughout corresponds to previously published Tiam-1 cDNA (See, Habets, G. G., van der Kammen, R. A., Stam, J. C., Michiels, F., and Collard, J. G. (1995) Oncogene 10, 1371–1376; NCBI Gen Bank Accession #U16296). To obtain missing C-terminal sequences, a PCR reaction employing oligonucleotides designed against the human Tiam-1 cDNA (See, Habets, G. G., van der Kammen, R. A., Stam, J. C., Michiels, F., and Collard, J. G. (1995) Oncogene 10, 1371–1376; NCBI Gen Bank Accession #U16296) 5'-CGGAATTCAGATTTCGACACATGATC-3' SEQ ID NO. 12 (sense) and 5'-TCGCCCGGGGCAGGTGACGCAGTCAGA-3' SEQ ID NO. 13 (antisense, contains SmaI site downstream of stop codon) as primers and a human hippocampal library (Clontech #HL3023b) as template produced a fragment containing nt 4458–5366 which was added to existing clones using the internal Eco47III (4487) site. A similar strategy using the antisense primer 5'-GATCCCGGGTCATGTTTCTGGTTCTGGGATCTCA GTGTTCAGTTTCCTG-3' SEQ ID No. 14 was used to add the KT3 epitope tag "PEPET (SEQ ID NO: 33)," a stop codon, and a SmaI site to the end of Tiam-1. To splice the two partial clones together, a PCR reaction using 5'-CGGAATTCCATGGGCCGCCTTGGAATCT-3' SEQ ID No. 15 (sense) and 5'-TCGCCCGGGCGTCAGCAGCACGATTAT-3' SEQ ID No.16 (antisense) as primers, and a human fetal brain cDNA library (Clontech #HL50156) as template produced a product spanning nt 2422–3189 which was cloned into pBS SK+(Stratagaene #212201) using EcoRI and SmaI. NcoI (472)–NcoI (2422) and StuI (3134)-SmaI fragments were ligated into this vector, creating full-length clones, with and without the KT3 tag.

It is note worthy that the isolated Tiam-1 sequence was altered from the published sequence. The 5' clone obtained from the library contained an insert of sequence 5'-GGTGAGCAGTTTACACTTTCATATACTCCCTGTCA TGTGCTTTGAAGGACTTTCTAGGGGCATCAAG-3' SEQ ID NO.17 in the upstream non-coding region at nt 105. Original clones from the Stratagene fetal brain library as well as all PCR products from Clontech hippocampal and brain libraries contained a difference in sequence from the published Tiam-1 cDNA ((See, Habets, G. G., van der Kammen, R. A., Stam, J. C., Michiels, F., and Collard, J. G. (1995) Oncogene 10, 1371–1376; NCBI Gen Bank Accession #U16296); a G at nt 3005 instead of a C, which therefore encodes a Gln in position 844 instead of a His. In addition, PCR introduced silent mutations G4739A and G5153A.

Example 5

Expression of Tiam-1 and Truncations

The following expression vectors were constructed and used to express the appropriate Tiam-1 constructs.

Full-length (178 kD) Tiam-1: A KT3-tagged 4792 basepair (bp) NcoI (472)-SmaI fragment was ligated into NcoI-SmaI-digested pAcC4 (See, Rubinfeld, B., et al. Cell 65, 1033–1042 (1991)): Bio/Technology 6:47–55 (derived from pAc436)).

135 kD Tiam-1: The 5' phosphorylated oligonucleotides 5'-GTCATGATGG-3' SEQ ID NO.18 and 5'-TCCATCATGACGGCC-3' SEQ ID No.19 were used as linkers to recircularize ApaI-EcoNI (1673)-digested pBS SK+-based full-length Tiam-1. The linker-created BspHI site and the vector-derived SpeI site were used to clone the 4006 bp fragment into NcoI-X baI-digested pAcC4 (See, Rubinfeld, B., et al. Cell 65, 1033–1042 (1991)).

106 kD Tiam-1: The NcoI (472)–NcoI (2422) fragment was removed from the full-length pAcC4-based expression vector.

85 kD Tiam-1: PCR using 5'-CTTGAATTCCACCATGGAAATCTGTCCAAAAG TCACT-3' SEQ ID No. 20 (sense) and 5'-TCGCCCGGGCGTCAGCAGCACGATTAT-3' SEQ ID No. 21 (antisense) as primers and the Stratagene Tiam-1 nt 2972–4657 clone as template was used to create an NcoI-StuI (3134) fragment that placed an ATG before nt 2972. The 2297 bp NcoI-SmaI was ligated into NcoI-SmaI-digested pAcC4 (See, Rubinfeld, B., et al. Cell 65, 1033–1042 (1991)).

66 kD Tiam-1: The 5' phosphorylated oligonucleotides 5'-CATGGACCAGAACCCATCTCC-3' SEQ ID NO. 22 and 5'-TGAGGAGATGGGTTCTGGTC-3' SEQ ID NO. 23 were used as linkers to recircularize NcoI (472)-Bsu36I (3534)-digested pBS SK+-based full-length Tiam-1. The linker-regenerated NcoI site and the vector-derived SpeI site were used to clone the 1761 bp fragment into NcoI-XbaI-digested pAcC4 (See, Rubinfeld, B., et al. Cell 65, 1033–1042 (1991)).

ΔPH versions of Tiam-1: The oligonucleotides 5'-GCCAGAACCAGAAACATGAC-3' SEQ ID NO.24 and 5'-CCGGGTCATGTTTCTGGTTCTGGC-3' SEQ ID NO.25 were used as linkers to recircularize Eco47III (4487) and XmaI-digested pAcC4-based expression vectors containing the 135 kD, 106 kD, 85 kD, and 66 kD versions of Tiam-1. These primers also restored the KT3 tag.

GST-PH domain fusion proteins: Products from PCR reactions using Tiam-1 cDNA as template and 5'-GAGGAATTCGATCTGAGCATGGGAGACCTG-3' SEQ ID NO.26 and 5'-CTGCTCGAGCTACTTATCACGCAGGATTGAATG-3' SEQ ID NO.27 (C-terminal PH domain) or 5'-CAGGAATTCGTGCGCAAGGCCGGCGCCCTG-3' SEQ ID NO.28 and 5'-GTGCTCGAGCTACGCAGTGGCGCAGGCAGAG TG-3' SEQ ID NO.29 (N-terminal PH domain) as primers were cloned into pGEX20T (See, Helin, K., Harlow, E. and Fattaey, A. (1993) Mol. Cell. Biol. 13, 6501–6508) using EcoRI and XhoI.

All Tiam-1 constructs, except for the GST fusions, were produced in baculoviurs-infected S. frugiperda-9 cells and were purified using KT3-mAb immunoaffinity chromatography. See, Schreurs, J., Yamamoto, R., Lyons, J., Munemitsu, S., Conroy, L., Clark, R., Takeda, Y., Krause, J. E., and Innis, M. (1995) J. Neurochem. 64, 1622–1631. GST fusion proteins were produced in E.coli and purified using glutathione-agarose. See, Smith, D. B. and Johnson, K. S, (1988) Gene 67,31–40.

Example 6

Stimulators of Tiam-1 Rac GEF Activity

The GEF activity of the various Tiam-1 constructs described above was determined in the presence and absence of certain compounds. The following assay was utilized. Reactions were conducted at room temperature in Buffer A (20 mM Hepes pH7.3, 50 mM NaCl, 2 mM DTT, 2 mM MgCl2). All proteins and compounds were diluted to 4× their final concentrations in Buffer A (GTPases were diluted in Buffer A containing 1 $\mu$M GDP). To dilute Ascorbyl Stearate, Ascorbyl Palmitate, and Stearic Acid, 25 mM ETOH solutions were slowly added to Buffer A while vortexing vigorously. Other lipids were resuspended in aqueous solution with vortexing and bath sonication and then diluted into Buffer A. Reactions were prepared and at time 0, $\lambda$-$^{32}$P-GTP (DuPont NEN #NEG006H) was added to 4.5 nM, and after 10 minutes reactions were stopped by filtering onto nitrocellulose filters (Millipore #HAWP02500) and immediately washed with wash buffer (25 mM Tris 7.5, 100 mM NaCl, 30 mM MgCl2). Bound $\lambda$-$^{32}$P-GTP was measured, using standard techniques.

Figure 3:
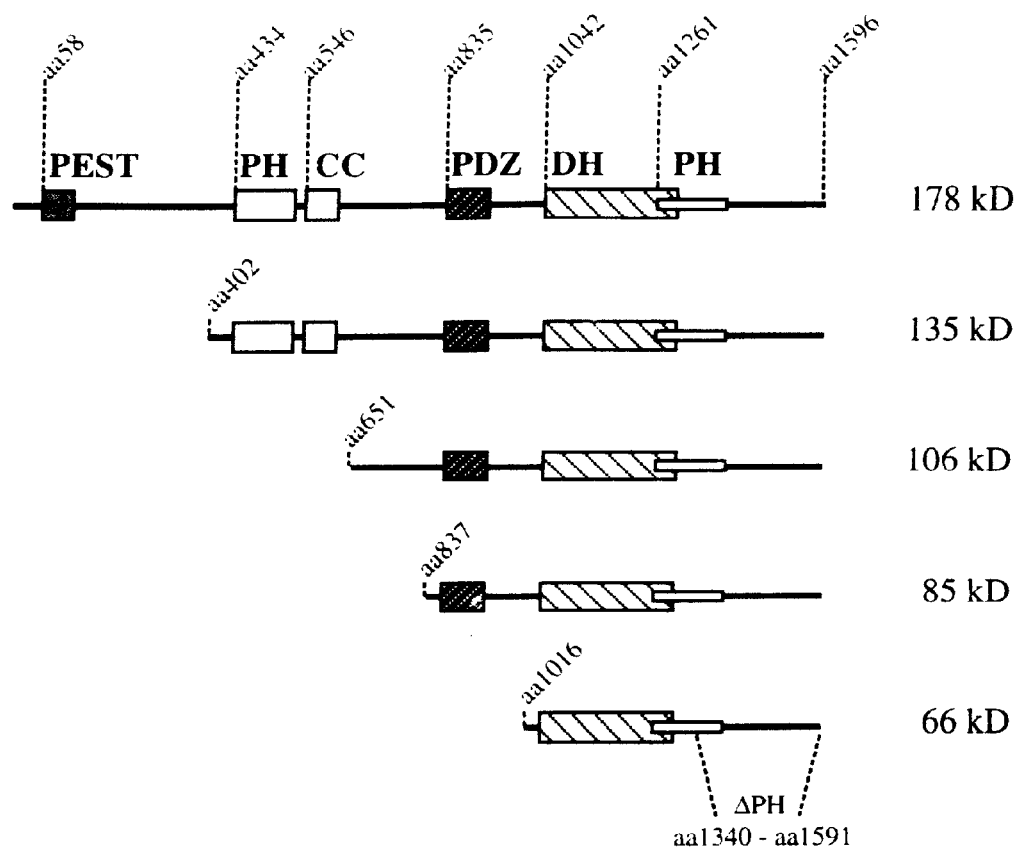
FIG. 3 shows the domain structures of full length Tiam-1, and truncations of the molecule.
Figure 4:
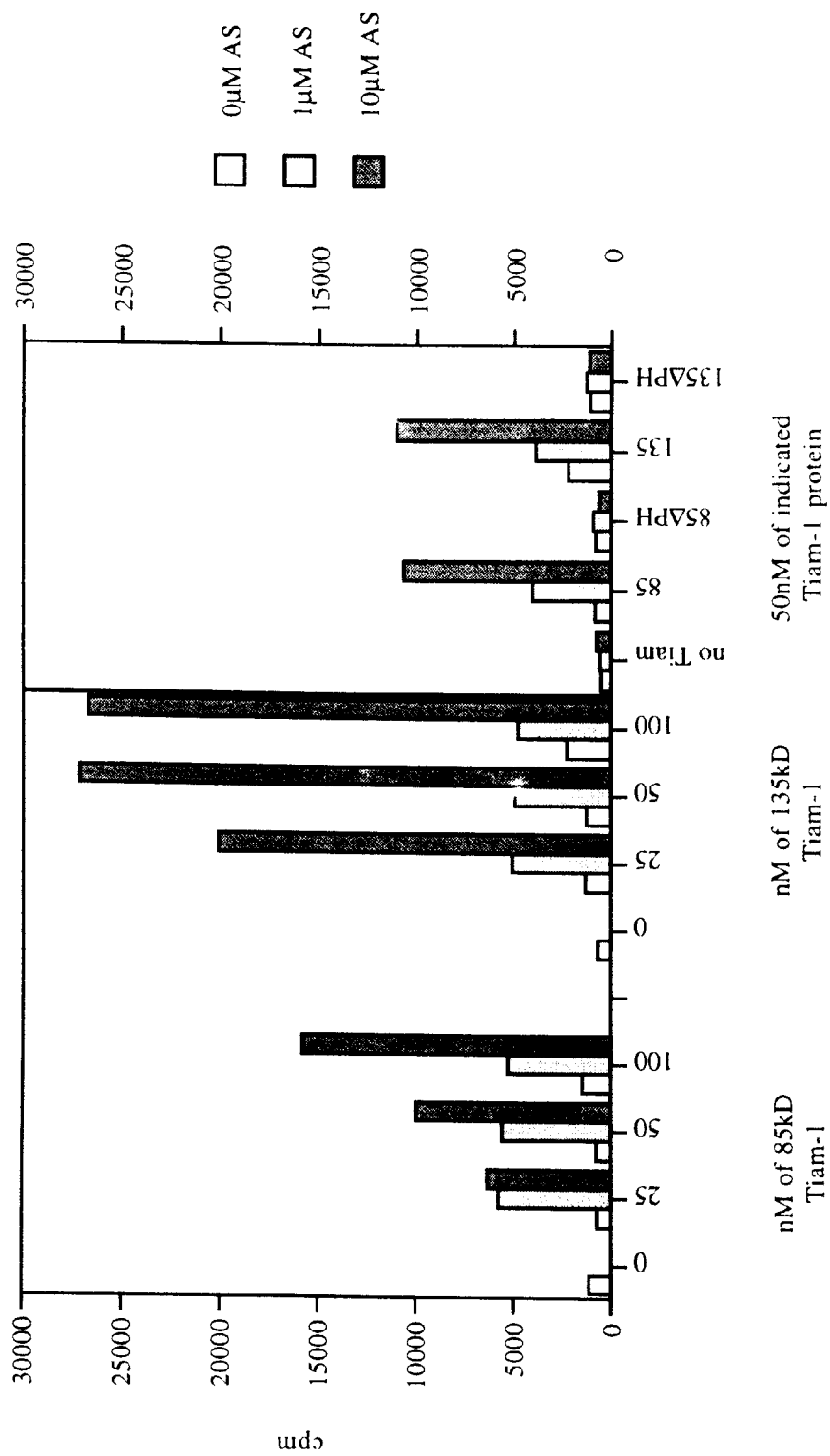
FIG. 4 shows the stimulatory effect of ascorbyl stearate on Rac exchange activity by various forms of truncated Tiam-1, the 85kd and 135 kD molecules.
Figure 5:
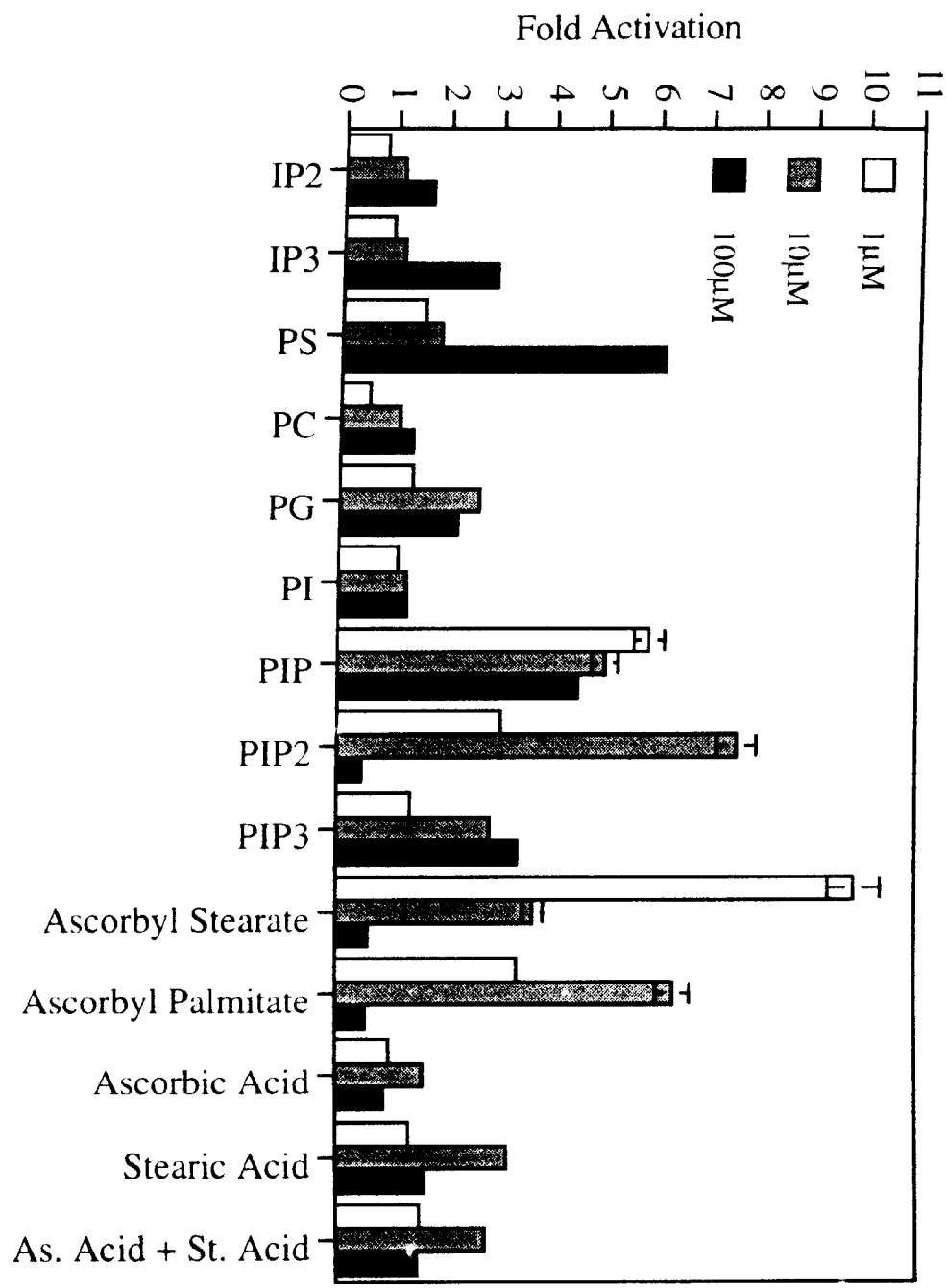
FIG. 5 shows the effects of certain ascorbyl compounds, inositol lipids and phospholipids on Tiam-1 stimulated Rac-GEF activity.

The 85 kD portion of human Tiam-1 protein was produced in insect cells and purified by affinity chromatography, as described above. This protein contained an intact PDZ domain, Dbl-homology (DH) domain and adjacent pleckstrin homology (PH) domain (FIG. 3). Using the above described assay, this truncation alone, at various concentrations, exhibited no GEF activity towards Rac 1 (FIG. 4). in contrast, ascorbyl stearate (AS) stimulated the rate of Tiam-1-mediated nucleotide exchange on Rac 1 (FIG. 4). Because AS has the potential to act as a detergent or a reducing agent, other detergents (nOG, TRITON X-100, NP40) and reducing agents (DTT, TCEP, or Tris (2-carboxyethyl)phosphine) were tested and shown not to significantly stimulate Tiam-1 GEE activity. Several other lipids were tested to determine the specificity of activation. Ascorbyl palmitate (AP), phosphatidylinositol-4-phosphate (PI(4)P), and phosphatidylinositol-4,5-bisphosphate (PI(4, 5)P2) significantly enhanced Tiam-1 activity; phosphatidylinositol-3,4,5-trisphosphate (PI(3,4,5)P3) and phosphatidylserine had weak effects; and phosphatidylglycerol, phosphatidylinositol and phosphatidyiholine had little or no effect (FIG. 5). As a control, experiments were run to determine if IP3, IP2, ascorbic acid, stearic acid and ascorbic acid with stearic acid were sufficient to activate the GEF activity of Tiam-1. The results showed that these reagents were incapable of stimulating GEF activity (FIG. 5).

Figure 6:
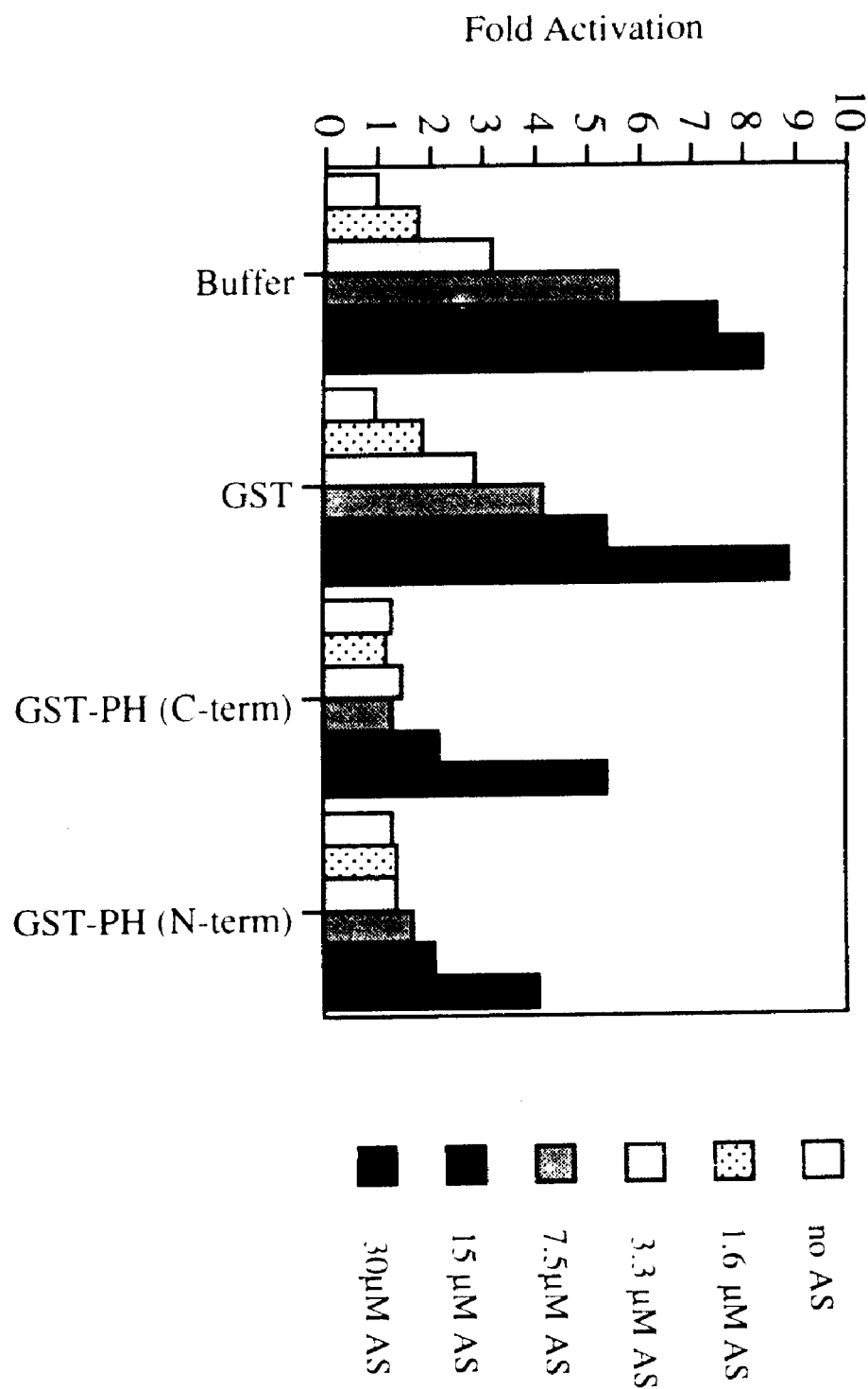
FIG. 6 shows the effects of ascorbyl sterate on Tiam-1 constructs that have PH and DH domains.

It has been previously reported that Tiam-1 has GEE activity in the absence absence of lipids. See, Michiels, F., Habets, G. G., Stam, J. C., van der Kammen, R. A., and Collard, J. G. (1995) *Nature* 375,338–340. Those studies used a miouse version containing additional upstream sequences, including the N-terminal PH domain and the coiled-coil region. To determine if upstream regions are necessary for expression of the DH domain GEF activity, the corresponding human construct was prepared (FIG. 3). This 135 kD Tiam-1 truncation shows weak GEF activity towards Rac in the absence of AS, but is still greatly stimulated by AS (FIG. 4). Other truncations of Tiam-1, all containing the DH and PH domains (FIG. 3), also exhibited AS stimulated GEF activity on Rac 1 (FIG. 6).

To determine if AS binding to the PH domain was responsible for activation of Tiam-1 GEF activity, sequences 3' of the Eco47III site were deleted, removing half of the C-terminal PH domain as well as the rest of the C-terminus (FIG. 3). These truncations of Tiam-1 were not activated by AS, including one that contained the N-terminal PH domain (FIG. 4). While it is possible that deleting the PH domain destroys activity of the DH domain altogether, similar truncations of the PH domain of the Dbl protein do not affect its GEF activity (See, Zheng, Y., Zangrilli, D., Cerione, R. A., and Eva, A. (1996). *J. Biol. Chem.* 271, 19017–19020). To further determine if the PH domains could bind to AS, GST-PH fusion proteins were included in the reaction. While GST alone did not affect AS-stimulated Tiam-1 exchange activity, both of the Tiam-1 GST-PH domain fusions reduced the effectiveness of AS (FIG. 6).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patents/patent applications and publications, cited above and in the figures are hereby incorporated by reference in the entirety.

From the foregoing description, one skilled in the art can easily ascertain the essential characteristics of this invention, and without departing from the spirit and scope thereof, can make various changes and modifications of the invention to adapt it to various usages and conditions.

What is claimed:

1. An isolated nucleic acid comprising a nucleotide sequence coding for a Rac-GEF polypeptide, wherein the isolated nucleic acid is set forth in SEQ ID NO:1.

2. The isolated nucleic acid of claim 1 which is human.

3. The isolated nucleic acid of claim 1, consisting of the nucleic acid sequence which codes for amino acid 1 to amino acid 710, as set forth in FIG. 1 SEQ ID NO:2.

4. The isolated nucleic acid of claim 1, wherein the nucleotide sequence is operably linked to an expression control sequence.

5. The isolated nucleic acid of claim 1, wherein the nucleic acid is DNA or RNA.

6. The isolated nucleic acid of claim 1, wherein the nucleic acid further comprises a detectable label.

7. A vector comprising the nucleic acid of claim 1.

8. A method of expressing in transformed host cells, a Rac-GEF polypeptide coded for by a nucleic acid, comprising culturing transformed host cells containing a nucleic acid according to claim 1 under conditions effective to express the polypeptide.

9. The method of claim 8, further comprising isolating the polypeptide.

10. An isolated nucleic acid comprising a nucleotide sequence encoding a RAC-GEF polypeptide, which hybridizes, or whose nucleic acid complement hybridizes, under stringent conditions to base pairs 900–1482 of the nucleotide sequence as set forth in FIG. 1 SEQ ID NO:1.

11. The isolated nucleic acid of claim 10 comprising at least 95% nucleotide sequence identity to base pairs 900–1482 of the nucleotide sequence set forth in SEQ ID NO:1.

12. The isolated nucleic acid of claim 10, wherein said nucleic acid codes for a polypeptide having a guanine nucleotide exchange activity, a specific binding affinity for a guanine nucleotide depleted Rac, or a cellular oncogenic transforming activity.

13. A method of expressing, in transformed host cells, a polypeptide coded for by a nucleic acid, comprising culturing transformed host cells containing a nucleic acid according to claim 10 under conditions effective to express the polypeptide.

14. A vector comprising the nucleic acid of claim 10.

15. An isolated nucleic acid comprising a nucleotide sequence encoding a RAC-GEF polypeptide, which hybridizes, or whose nucleic acid complement hybridizes, under stringent conditions to the nucleotide sequence of SEQ ID NO: 1.

* * * * *